US007223473B2

(12) United States Patent
Jiang et al.

(10) Patent No.: US 7,223,473 B2
(45) Date of Patent: May 29, 2007

(54) POROUS INORGANIC/ORGANIC HYBRID PARTICLES FOR CHROMATOGRAPHIC SEPARATIONS AND PROCESS FOR THEIR PREPARATION

(75) Inventors: Zhiping Jiang, Westford, MA (US); Raymond P. Fisk, Norton, MA (US); John O'Gara, Ashland, MA (US); Thomas H. Walter, Ashland, MA (US); Kevin D. Wyndham, Allston, MA (US)

(73) Assignee: Waters Investments Limited, New Castle, DE (US)

( * ) Notice: Subject to any disclaimer, the term of this patent is extended or adjusted under 35 U.S.C. 154(b) by 26 days.

(21) Appl. No.: 10/744,598

(22) Filed: Dec. 22, 2003

(65) Prior Publication Data

US 2004/0191516 A1 Sep. 30, 2004

Related U.S. Application Data

(60) Division of application No. 09/924,399, filed on Aug. 7, 2001, now Pat. No. 6,686,035, which is a continuation-in-part of application No. 09/858,087, filed on May 14, 2001, now abandoned, which is a continuation of application No. 09/244,795, filed on Feb. 5, 1999, now abandoned.

(51) Int. Cl.
*B32B 5/16* (2006.01)
*B01D 15/08* (2006.01)

(52) U.S. Cl. .................... 428/403; 210/198.2; 428/407

(58) Field of Classification Search ................ 428/402, 428/403, 407; 210/263, 509, 500.1, 198.2
See application file for complete search history.

(56) References Cited

U.S. PATENT DOCUMENTS

| 3,892,678 | A | 7/1975 | Halasz et al. ................ 252/426 |
| 3,935,299 | A | 1/1976 | Kiselev et al. ............... 423/338 |
| 4,017,528 | A | 4/1977 | Unger et al. ............. 260/448.8 |
| 4,104,363 | A | 8/1978 | Vozka et al. ................ 423/338 |
| 4,169,069 | A | 9/1979 | Unger et al. ................ 252/316 |
| 4,724,207 | A | 2/1988 | Hou et al. ................... 435/180 |
| 4,775,520 | A | 10/1988 | Unger et al. ................ 423/335 |
| 4,889,632 | A | 12/1989 | Svec et al. |
| 4,911,903 | A | 3/1990 | Unger et al. ................ 423/335 |
| 4,923,610 | A | 5/1990 | Svec et al. |
| 4,952,349 | A | 8/1990 | Svec et al. |
| 4,983,369 | A | 1/1991 | Barder et al. ................ 423/338 |
| 5,068,387 | A | 11/1991 | Kleyer et al. ................ 556/485 |
| 5,071,565 | A | 12/1991 | Fritz et al. ................... 210/692 |
| 5,108,595 | A | 4/1992 | Kirkland et al. .......... 210/198.2 |
| 5,137,627 | A | 8/1992 | Feibush ................... 210/198.2 |
| 5,154,822 | A | 10/1992 | Simpson et al. ......... 210/198.2 |
| 5,194,333 | A | 3/1993 | Ohnaka et al. .............. 428/405 |
| 5,256,386 | A | 10/1993 | Nystrom et al. ............. 423/338 |
| 5,271,833 | A | 12/1993 | Funkenbusch et al. |
| 5,374,755 | A | 12/1994 | Neue et al. .................. 556/400 |
| 5,378,790 | A * | 1/1995 | Michalczyk et al. .......... 528/35 |
| 5,425,930 | A | 6/1995 | Anderson .................... 423/338 |
| 5,453,185 | A | 9/1995 | Frechet et al. |
| 5,498,678 | A | 3/1996 | Steffier ........................ 526/200 |
| 5,548,051 | A | 8/1996 | Michalczyk et al. |
| 5,558,849 | A | 9/1996 | Sharp .......................... 423/338 |
| 5,565,142 | A | 10/1996 | Deshpande et al. ....... 252/315.2 |
| 5,624,875 | A | 4/1997 | Nakanishi et al. ............. 501/39 |
| 5,637,135 | A | 6/1997 | Ottenstein et al. ............. 96/101 |
| 5,650,474 | A | 7/1997 | Yamaya et al. |
| 5,651,921 | A | 7/1997 | Kaijou ........................ 252/309 |
| 5,667,674 | A | 9/1997 | Hanggi et al. ............ 210/198.2 |
| 5,728,457 | A | 3/1998 | Frechet et al. |
| 5,734,020 | A | 3/1998 | Wong .......................... 530/350 |
| 5,856,379 | A | 1/1999 | Shiratsuchi et al. ......... 523/209 |
| 5,869,152 | A | 2/1999 | Colon ........................ 428/34.4 |
| 5,965,202 | A | 10/1999 | Taylor-Smith et al. ....... 427/245 |
| 5,976,479 | A | 11/1999 | Alcaraz et al. .............. 423/335 |
| 6,017,632 | A | 1/2000 | Pinnavaia et al. |
| 6,090,477 | A | 7/2000 | Burchell et al. |
| 6,136,187 | A | 10/2000 | Zare et al. |
| 6,183,867 | B1 * | 2/2001 | Barthel et al. .............. 428/403 |
| 6,207,098 | B1 | 3/2001 | Nakanishi et al. |
| 6,210,570 | B1 | 4/2001 | Holloway |
| 6,238,565 | B1 | 5/2001 | Hatch |
| 6,248,686 | B1 | 6/2001 | Inagaki et al. |

(Continued)

FOREIGN PATENT DOCUMENTS

| EP | 0 852 334 A1 | 7/1998 |
| JP | 07247180 | 9/1995 |
| JP | 2893104 | 3/1999 |
| WO | 00/45951 | 8/2000 |
| WO | 03/014450 | 2/2003 |
| WO | 03/022392 | 3/2003 |
| WO | 2004/041398 | 5/2004 |
| WO | PCT/US05/25106 | 7/2005 |

OTHER PUBLICATIONS

Neue, U.D. et al., "Use of high-performance LC packings from pH 1 to Ph 12," *American LaAoratory*, Nov. 1999, p. 36-39.

(Continued)

*Primary Examiner*—H. Thi Le
(74) *Attorney, Agent, or Firm*—Edwards Angell Palmer & Dodge LLP; Peter C. Lauro, Esq.

(57) ABSTRACT

Novel material for chromatographic separations, processes for its preparation, and separations devices containing the chromatographic material. In particular, the disclosure describes porous inorganic/organic hybrid particles having a chromatographically-enhancing pore geometry, which desirably may be surface modified, and that offer more efficient chromatographic separations than that known in the art.

21 Claims, No Drawings

U.S. PATENT DOCUMENTS

| | | | |
|---|---|---|---|
| 6,271,292 B1 | 8/2001 | Mager et al. | 524/261 |
| 6,277,304 B1 | 8/2001 | Wei et al. | |
| 6,281,257 B1 | 8/2001 | Ma et al. | |
| 6,288,198 B1 * | 9/2001 | Mechtel et al. | 528/28 |
| 6,313,219 B1 | 11/2001 | Taylor-Smith | 524/853 |
| 6,380,266 B1 | 4/2002 | Katz et al. | |
| 6,395,341 B1 | 5/2002 | Arakawa et al. | 427/419.1 |
| 6,465,387 B1 | 10/2002 | Pinnavaia et al. | 502/158 |
| 6,476,098 B1 | 11/2002 | Arakawa et al. | 523/206 |
| 6,528,167 B2 * | 3/2003 | O'Gara | 428/405 |
| 6,686,035 B2 * | 2/2004 | Jiang et al. | 428/304.4 |
| 2003/0150811 A1 | 8/2003 | Walter et al. | |

OTHER PUBLICATIONS

Reynolds, K.J. et al., "SuAmicron sized organo-silica spheres for capillary electrochromatography," *J. Liq. Chrom & Rel. Technol.*, 2000, 23(1):161-173.

Unger, K.K. et al., "Recent developments in the evaluation of chemically Aonded silica packings for liquid chromatography," *J. Chromatogr.* 1976, 125(1):115-127.

Hileman, F.D. et al. Anal. Chem. 1973, 45, pp. 1126.

Hanson, M. J. Chromatography A, 1993, 656, pp. 369.

Petro, M. et al., Chromatographia, 1993, 9/10, pp. 549.

Goldstein, A. et al., J. of Mat. Sci. Letters, 1997, 16, 310.

Tamaki, Polymer Bull, 1997, 39, pp. 303.

Dulay, M.T. et al. Anal. Chem. 1998, 70, pp. 5103.

Asiaie, R. et al. J. Chromatography A. 1998, 806, pp. 251.

Xin, B. et al. Electrophoresis 1999, 20, pp. 67.

Tang, Q. et al. J. Chromatography A. 1999, 837, pp. 35.

Perry, R. J. Chemtech 1999, pp. 39.

Grun, M. et al. Microporous and Mesoporous Materials 1999, 27, pp. 207.

Inagaki, S. et al. J. Am. Chem. Soc. 1999, 121, 9611.

* cited by examiner

POROUS INORGANIC/ORGANIC HYBRID PARTICLES FOR CHROMATOGRAPHIC SEPARATIONS AND PROCESS FOR THEIR PREPARATION

This application is a divisional application of Ser. No. 09/924,399 filed on Aug. 7, 2001, now U.S. Pat. No. 6,686,035 Allowed, which in turn is a continuation-in-part application of Ser. No. 09/858,087, filed May 14, 2001, Abandoned, which in turn is a continuation of Ser. No. 09/244,795, filed Feb. 5, 1999, Abandoned. The disclosures of each of the aforementioned applications are incorporated herein in their entireties by this reference.

BACKGROUND OF THE INVENTION

Packing materials for liquid chromatography (LC) are generally classified into two types: organic materials, e.g., polydivinylbenzene, and inorganic materials typified by silica. Many organic materials are chemically stable against strongly alkaline and strongly acidic mobile phases, allowing flexibility in the choice of mobile phase pH. However, organic chromatographic materials generally result in columns with low efficiency, leading to inadequate separation performance, particularly with low molecular-weight analytes. Furthermore, many organic chromatographic materials shrink and swell when the composition of the mobile phase is changed. In addition, most organic chromatographic materials do not have the mechanical strength of typical chromatographic silicas.

Due in large part to these limitations, silica is the material most widely used in High Performance Liquid Chromatography (HPLC). The most common applications employ silica that has been surface-derivatized with an organic functional group such as octadecyl ($C_{18}$), octyl ($C_8$), phenyl, amino, cyano, etc. As stationary phases for HPLC, these packing materials result in columns that have high efficiency and do not show evidence of shrinking or swelling.

Silica is characterized by the presence of silanol groups on its surface. During a typical derivatization process such as reaction with octadecyldimethylchlorosilane, at least 50% of the surface silanol groups remain unreacted. These residual silanol groups interact with basic and acidic analytes via ion exchange, hydrogen bonding and dipole/dipole mechanisms. The residual silanol groups create problems including increased retention, excessive peak tailing and irreversible adsorption of some analytes. Another drawback with silica-based columns is their limited hydrolytic stability. First, the incomplete derivatization of the silica leaves patches of bare silica surface which can be readily dissolved under alkaline conditions, generally pH>8.0, leading to the subsequent collapse of the chromatographic bed. Secondly, the bonded phase can be stripped off the surface under acidic conditions, generally pH<2.0, and eluted off the column by the mobile phase, causing loss of analyte retention, and an increase in the concentration of surface silanol groups.

To overcome the problems of residual silanol group activity and hydrolytic instability of silica-based stationary phases, many methods have been tried including use of ultrapure silica, carbonized silica, coating of the silica surface with polymeric materials, endcapping free silanol groups with a short-chain reagent such as trimethylsilane, and the addition of suppressors such as amines to the eluant. These approaches have not proven to be completely satisfactory in practice.

One approach is disclosed in U.S. Pat. No. 4,017,528. A process for preparing a "hybrid" silica is described wherein an alkyl functionality is coupled into both the skeleton structure and the surface of the silica. According to the '528 patent, the hybrid silica can be prepared by two methods. In the first method, a mixture of tetraethoxysilane (TEOS) and an organotriethoxysilane, e.g., alkyltriethoxysilane, is co-hydrolyzed in the presence of an acid catalyst to form a liquid material containing polyorganoethoxysiloxane (POS) oligomers, e.g., polyalkylethoxysiloxane oligomers. Then, the POS is suspended in an aqueous medium and gelled into porous particles in the presence of a base catalyst. In the second method, the material is prepared by a similar procedure except that the suspension droplet is a mixture of organotriethoxysilane, e.g., alkyltriethoxysilane, and polyethoxysiloxane (PES) oligomers; the latter is prepared by partial hydrolysis of TEOS.

There are several problems associated with the '528 hybrid material. First, these hybrid materials contain numerous micropores, i.e., pores having a diameter below 34 Å. It is known that such micropores inhibit solute mass transfer, resulting in poor peak shape and band broadening.

Second, the pore structure of the '528 hybrid material is formed because of the presence of ethanol (a side product of the gelation process) within the suspension oil droplets. The pore volume is controlled by the molecular weight of the POS or PES. The lower the molecular weight of the POS or PES, the more ethanol is generated during the gelation reaction, and subsequently a larger pore volume is produced. However, part of the ethanol generated during the gelation is able to diffuse into the aqueous phase by partition. If the amount of the ethanol generated within the suspension droplets is too great, the partition of the ethanol will cause the structure of the droplets to collapse, forming irregularly-shaped particles as opposed to spherical particles. Therefore, the strategy to control the pore volume of the hybrid material described in the '528 patent has certain limitations, particularly for preparing highly spherical hybrid materials with a pore volume greater than about 0.8 $cm^3/g$. It is well known in the art that irregularly-shaped materials are generally more difficult to pack than spherical materials. It is also known that columns packed with irregularly-shaped materials generally exhibit poorer packed bed stability than spherical materials of the same size.

Thirdly, the '528 hybrid materials are characterized by an inhomogeneous particle morphology, which contributes to undesirable chromatographic properties, including poor mass transfer properties for solute molecules. This is a consequence of the gelation mechanism, where the base catalyst reacts rapidly near the surface of the POS droplet, forming a "skinned" layer having very small pores. Further gelation in the interior of the droplet is then limited by the diffusion of catalyst through this outer layer towards the droplet center, leading to particles having skeletal morphologies and hence pore geometries, e.g., "shell shaped", which can vary as a function of location between the particle center and outer layer.

SUMMARY OF THE INVENTION

The present invention relates to a novel material for chromatographic separations, processes for its preparation, and separations devices containing the chromatographic material. In particular, one aspect of the invention is a porous inorganic/organic hybrid material, comprising porous inorganic/organic hybrid particles having a chromatographically-enhancing pore geometry.

Another aspect of the invention is a porous inorganic/organic hybrid material, comprising porous inorganic/organic hybrid particles having a chromatographically-enhancing pore geometry. The particles are surface modified with a surface modifier having the formula $Z_a(R')_b Si$—R, where Z=Cl, Br, I, $C_1$–$C_5$ alkoxy, dialkylamino or trifluoromethanesulfonate; a and b are each an integer from 0 to 3 provided that a+b=3; R' is a $C_1$–$C_6$ straight, cyclic or branched alkyl group, and R is a functionalizing group.

An additional aspect of the invention is a method of preparation of porous inorganic/organic hybrid particles having a chromatographically-enhancing pore geometry, comprising the steps of
  a) forming porous inorganic/organic hybrid particles,
  b) modifying the pore structure of said porous particles.

In another aspect of the invention, the invention is a method of preparation of porous inorganic/organic hybrid particles having a chromatographically-enhancing pore geometry, comprising the steps of
  a) forming porous inorganic/organic hybrid particles,
  b) modifying the pore structure of the porous particles, and
  c) surface modifying the porous particles
wherein the surface modification step includes surface modifying the porous particles with a surface modifier having the formula $Z_a(R')_b Si$—R, where Z=Cl, Br, I, $C_1$–$C_5$ alkoxy, dialkylamino or trifluoromethanesulfonate; a and b are each an integer from 0 to 3 provided that a+b=3; R' is a $C_1$–$C_6$ straight, cyclic or branched alkyl group, and R is a functionalizing group.

Yet another aspect of the invention is a separations device having a stationary phase comprising porous inorganic/organic hybrid particles having a chromatographically-enhancing pore geometry.

Another aspect of the invention is a separations device having a stationary phase comprising porous inorganic/organic hybrid particles having a chromatographically-enhancing pore geometry, wherein the particles have been surface modified with a surface modifier having the formula $Z_a(R')_b Si$—R, where Z=Cl, Br, I, $C_1$–$C_5$ alkoxy, dialkylamino or trifluoromethanesulfonate; a and b are each an integer from 0 to 3 provided that a+b=3; R' is a $C_1$–$C_6$ straight, cyclic or branched alkyl group, and R is a functionalizing group.

In yet another aspect, the invention is a chromatographic column having improved lifetime, comprising
  a) a column having a cylindrical interior for accepting a packing material, and
  b) a packed chromatographic bed comprising porous inorganic/organic hybrid particles having a chromatographically-enhancing pore geometry of the formula $SiO_2/(R^2_p R^4_q SiO_t)_n$ or $SiO_2/[R^6(R^2_r SiO_t)_m]_n$ wherein $R^2$ and $R^4$ are independently $C_1$–$C_{18}$ aliphatic or aromatic moieties, $R^6$ is a substituted or unsubstituted $C_1$–$C_{18}$ alkylene, alkenylene, alkynylene or arylene moiety bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, said porous hybrid silica chromatographic matrix having a chromatographically-enhancing pore geometry and average pore diameters of about 100 to 300 Å, and said porous particles of hybrid silica have been surface modified.

In yet another aspect, the invention is a chromatographic column having improved lifetime, comprising
  a) a column having a cylindrical interior for accepting a packing material, and
  b) a packed chromatographic bed comprising porous inorganic/organic hybrid particles having a chromatographically-enhancing pore geometry that have been surface modified with a surface modifier having the formula $Z_a(R')_b Si$—R, where Z=Cl, Br, I, $C_1$–$C_5$ alkoxy, dialkylamino or trifluoromethanesulfonate; a and b are each an integer from 0 to 3 provided that a+b=3; R' is a $C_1$–$C_6$ straight, cyclic or branched alkyl group, and R is a functionalizing group.

Another aspect of the invention is a method of preparation of porous particles of hybrid silica having a chromatographically-enhancing pore geometry, comprising the steps of
  a) prepolymerizing a mixture of one or more organoalkoxysilanes and a tetraalkoxysilane in the presence of an acid catalyst to produce a polyorganoalkoxysiloxane;
  b) preparing an aqueous suspension of said polyorganoalkoxysiloxane, said suspension further comprising a surfactant or combination of surfactants, and gelling in the presence of a base catalyst so as to produce porous particles; and
  c) modifying the pore structure of said porous particles by hydrothermal treatment, thereby preparing porous particles of hybrid silica having a chromatographically-enhancing pore geometry.

In an additional aspect, the invention is a porous particle of hybrid silica having a chromatographically-enhancing pore geometry, produced by the process of
  a) prepolymerizing a mixture of one or more organoalkoxysilanes and a tetraalkoxysilane in the presence of an acid catalyst to produce a polyorganoalkoxysiloxane;
  b) preparing an aqueous suspension of said polyorganoalkyloxysiloxane, said suspension further comprising a surfactant or a combination of surfactants, and gelling in the presence of an base catalyst so as to produce porous particles; and
  c) modifying the pore structure of said porous particles by hydrothermal treatment, thereby producing porous particles of hybrid silica having a chromatographically-enhancing pore geometry.

DETAILED DESCRIPTION OF THE INVENTION

The present invention will be more fully illustrated by reference to the definitions set forth below.

The language "chromatographically-enhancing pore geometry" includes the geometry of the pore configuration of the presently-disclosed porous inorganic/organic hybrid particles, which has been found to enhance the chromatographic separation ability of the material, e.g., as distinguished from other chromatographic media in the art. For example, a geometry can be formed, selected or constructed, and various properties and/or factors can be used to determine whether the chromatographic separations ability of the material has been "enhanced", e.g., as compared to a geometry known or conventionally used in the art. Examples of these factors include high separation efficiency, longer column life, and high mass transfer properties (as evidenced by, e.g., reduced band spreading and good peak shape.) These properties can be measured or observed using art-recognized techniques. For example, the chromatographically-enhancing pore geometry of the present porous inorganic/organic hybrid particles is distinguished from the prior art particles by the absence of "ink bottle" or "shell shaped" pore geometry or morphology, both of which are undesirable because they, e.g., reduce mass transfer rates, leading to lower efficiencies.

Chromatographically-enhancing pore geometry is found in hybrid particles containing only a small population of micropores. A small population of micropores is achieved in hybrid particles when all pores of a diameter of about <34 Å contribute less than about 110 m$^2$/g to the specific surface area of the particle. Hybrid materials with such a low micropore surface area give chromatographic enhancements including high separation efficiency and good mass transfer properties (as evidenced by, e.g., reduced band spreading and good peak shape). Micropore surface area is defined as the surface area in pores with diameters less than or equal to 34 Å, determined by mulitpoint nitrogen sorption analysis from the adsorption leg of the isotherm using the BJH method.

"Hybrid", i.e., as in "porous inorganic/organic hybrid particles" includes inorganic-based structures wherein an organic functionality is integral to both the internal or "skeletal" inorganic structure as well as the hybrid material surface. The inorganic portion of the hybrid material may be, e.g., alumina, silica, titanium or zirconium oxides, or ceramic material; in a preferred embodiment, the inorganic portion of the hybrid material is silica. As noted before, exemplary hybrid materials are shown in U.S. Pat. No. 4,017,528, the text of which is incorporated herein by reference. In a preferred embodiment where the inorganic portion is silica, "hybrid silica" refers to a material having the formula $SiO_2/(R^2_pR^4_qSiO_t)_n$ or $SiO_2/[R^6(R^2_rSiO_t)_m]_n$ wherein $R^2$ and $R^4$ are independently $C_1$–$C_{18}$ aliphatic or aromatic moieties (which may additionally be substituted with alkyl, aryl, cyano, amino, hydroxyl, diol, nitro, ester, ion exchange or embedded polar functionalities), $R^6$ is a substituted or unsubstituted $C_1$–$C_{18}$ alkylene, alkenylene, alkynylene or arylene moiety bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, more preferably, 0.1 to 1, and even more preferably 0.2 to 0.5. $R^2$ may be additionally substituted with a functionalizing group R.

The term "functionalizing group" includes organic functional groups which impart a certain chromatographic functionality to a chromatographic stationary phase, including, e.g., octadecyl ($C_{18}$) or phenyl. Such functionalizing groups are present in, e.g., surface modifiers such as disclosed herein which are attached to the base material, e.g., via derivatization or coating and later crosslinking, imparting the chemical character of the surface modifier to the base material. In an embodiment, such surface modifiers have the formula $Z_a(R')_bSi$—R, where Z=Cl, Br, I, $C_1$–$C_5$ alkoxy, dialkylamino, e.g., dimethylamino, or trifluoromethanesulfonate; a and b are each an integer from 0 to 3 provided that a+b=3; R' is a $C_1$–$C_6$ straight, cyclic or branched alkyl group, and R is a functionalizing group. R' may be, e.g., methyl, ethyl, propyl, isopropyl, butyl, t-butyl, sec-butyl, pentyl, isopentyl, hexyl or cyclohexyl; preferably, R' is methyl.

The porous inorganic/organic hybrid particles possess both organic groups and silanol groups which may additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later crosslinking, imparting the chemical character of the surface modifier to the base material. In one embodiment, the organic groups of the hybrid particle react to form an organic covalent bond with a surface modifier. The modifiers can form an organic covalent bond to the particle's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds.

In another embodiment, silanol groups are surface modified with compounds having the formula $Z_a(R')_bSi$—R, where Z=Cl, Br, I, $C_1$–$C_5$ alkoxy, dialkylamino, e.g., dimethylamino, or trifluoromethanesulfonate; a and b are each an integer from 0 to 3 provided that a+b=3; R' is a $C_1$–$C_6$ straight, cyclic or branched alkyl group, and R is a functionalizing group. R' may be, e.g., methyl, ethyl, propyl, isopropyl, butyl, t-butyl, sec-butyl, pentyl, isopentyl, hexyl or cyclohexyl; preferably, R' is methyl. In certain embodiments, the organic groups may be similarly functionalized.

The functionalizing group R may include alkyl, aryl, cyano, amino, diol, nitro, cation or anion exchange groups, or embedded polar functionalities. Examples of suitable R functionalizing groups include $C_1$–$C_{30}$ alkyl, including $C_1$–$C_{20}$, such as octyl ($C_8$), octadecyl ($C_{18}$), and triacontyl ($C_{30}$); alkaryl, e.g., $C_1$–$C_4$-phenyl; cyanoalkyl groups, e.g., cyanopropyl; diol groups, e.g., propyldiol; amino groups, e.g., aminopropyl; and alkyl or aryl groups with embedded polar functionalities, e.g., carbamate functionalities such as disclosed in U.S. Pat. No. 5,374,755, the text of which is incorporated herein by reference. Such groups include those of the general formula

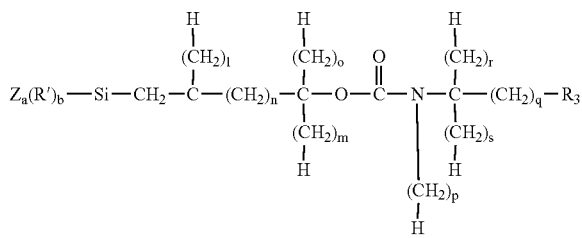

wherein l, m, o, r, and s are 0 or 1, n is 1, 2 or 3 p is 0, 1, 2, 3 or 4 and q is an integer from 0 to 19; $R_3$ is selected from the group consisting of hydrogen, alkyl, cyano and phenyl; and Z, R', a and b are defined as above. Preferably, the carbamate functionality has the general structure indicated below:

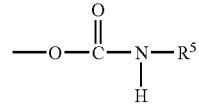

wherein $R^5$ may be, e.g., cyanoalkyl, t-butyl, butyl, octyl, dodecyl, tetradecyl, octadecyl, or benzyl. Advantageously, $R^5$ is octyl, dodecyl, or octadecyl. In a preferred embodiment, the surface modifier may be an organotrihalosilane, such as octyltrichlorosilane or octadecyltrichlorosilane. In an additional preferred embodiment, the surface modifier may be a halopolyorganosilane, such as octyldimethylchlorosilane or octadecyldimethylchlorosilane.

In another embodiment, the hybrid particle's organic groups and silanol groups are both surface modified or derivatized. In another embodiment, the particles are surface modified by coating with a polymer. In certain embodiments, surface modification by coating with a polymer is used in conjunction with silanol group modification, organic group modification, or both silanol and organic group modification.

The term "aliphatic group" includes organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl, and the like. As used herein, the term "nitro" means $-NO_2$; the term "halogen" designates $-F$, $-Cl$, $-Br$ or $-I$; the term "thiol" means SH; and the term "hydroxyl" means $-OH$. Thus, the term "alkylamino" as used herein means an alkyl group, as defined above, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, preferably from 1 to about 6 carbon atoms.

The term "alicyclic group" includes closed ring structures of three or more carbon atoms. Alicyclic groups include cycloparaffins or naphthenes which are saturated cyclic hydrocarbons, cycloolefins which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, $-CF_3$, $-CN$, or the like.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, $-CF_3$, $-CN$, or the like. Suitable heteroaromatic and heteroalicyclic groups generally will have 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The term "aromatic group" includes unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, $-CF_3$, $-CN$, or the like.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone, e.g., $C_1-C_{30}$ for straight chain or $C_3-C_{30}$ for branched chain. In certain embodiments, a straight chain or branched chain alkyl has 20 or fewer carbon atoms in its backbone, e.g., $C_1-C_{20}$ for straight chain or $C_3-C_{20}$ for branched chain, and more preferably 18 or fewer. Likewise, preferred cycloalkyls have from 4–10 carbon atoms in their ring structure, and more preferably have 4–7 carbon atoms in the ring structure. The term "lower alkyl" refers to alkyl groups having from 1 to 6 carbons in the chain, and to cycloalkyls having from 3 to 6 carbons in the ring structure.

Moreover, the term "alkyl" (including "lower alkyl") as used throughout the specification and claims includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl (benzyl).

The term "aryl" includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3separate or fused rings and from 6 to about 18 carbon ring atoms, e.g., O-benzyl.

The term "amino," as used herein, refers to an unsubstituted or substituted moiety of the formula —$NR_aR_b$, in which $R_a$ and $R_b$ are each independently hydrogen, alkyl, aryl, or heterocyclyl, or $R_a$ and $R_b$, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of $R_a$ and $R_b$, is further substituted with an amino group.

The present porous inorganic/organic hybrid particles having a chromatographically-enhancing pore geometry generally have a specific surface area, as measured by $N_2$ sorption analysis, of about 50 to 800 m$^2$/g, preferably about 75 to 600 m$^2$/g, more preferably about 100 to 200 m$^2$/g. The specific pore volume of the particles is generally about 0.25 to 1.5 cm$^3$/g, preferably about 0.4 to 1.2 cm$^3$/g, more preferably about 0.5 to 1.0 cm$^3$/g. The porous inorganic/organic hybrid particles having a chromatographically-enhancing pore geometry have an average pore diameter of generally about 50 to 500 Å, preferably about 60 to 500 Å, more preferably about 100 to 300 Å. The micropore surface area is less than about 110 m$^2$/g, preferably less than about 105 m$^2$/g, more preferably less than about 80 m$^2$/g, and still more preferably less than about 50 m$^2$/g.

Porous inorganic/organic hybrid particles having a chromatographically-enhancing pore geometry may be made as described below and in the specific instances illustrated in the Examples. Porous spherical particles of hybrid silica may, in a preferred embodiment, be prepared by a multi-step process. In the first step, one or more organoalkoxysilanes such as methyltriethoxysilane, and a tetraalkoxysilane such as tetraethoxysilane (TEOS) are prepolymerized to form a polyorganoalkoxysiloxane (POS), e.g., polyalkylalkoxysiloxane, by co-hydrolyzing a mixture of the two or more components in the presence of an acid catalyst. In the second step, the POS is suspended in an aqueous medium in the presence of a surfactant or a combination of surfactants and gelled into porous spherical particles of hybrid silica using a base catalyst. In the third step, the pore structure of the hybrid silica particles is modified by hydrothermal treatment, producing an intermediate hybrid silica product which may be used for particular purposes itself, or desirably may be further processed below. The above three steps of the process allow-much better control of the particle sphericity, morphology, pore volume and pore sizes than those described in the prior art, and thus provide the chromatographically-enhancing pore geometry.

In one embodiment of the invention, the surface organic groups of the hybrid silica are derivatized or modified in a subsequent step via formation of an organic covalent bond between the particle's organic group and the modifying reagent. Alternatively, the surface silanol groups of the hybrid silica are derivatized or modified into siloxane functional groups, such as by reacting with an organotrihalosilane, e.g., octadecyltrichlorosilane, or a halopolyorganosilane, e.g., octadecyldimethylchlorosilane. Alternatively, the surface organic and silanol groups of the hybrid silica are both derivatized or modified. The surface of the thus-prepared material is then covered by the organic groups, e.g., alkyl, embedded during the gelation and the organic groups added during the derivatization process or processes. The surface coverage by the overall organic groups is higher than in conventional silica-based packing materials, and therefore the surface concentration of the remaining silanol groups in the hybrid silica is smaller. The resulting material, used as a stationary phase for LC, shows excellent peak shape for basic analytes, and better stability to alkaline mobile phases than silica-based packing materials.

Where the prepolymerization step involves co-hydrolyzing a mixture of the two or more components in the presence of an acid catalyst, the content of the organoalkoxysilane, e.g., organotrialkoxysilane can be varied, e.g., from about 0.03 to about 1.0 mole per mole, or more preferably, about 0.2 to about 0.5 mole per mole, of the tetraalkoxysilane. The amount of the water used for the hydrolysis can be varied, e.g., from 1.10 to 1.35 mole per mole of the silane. The silane, water and the ethanol mixture, in the form of a homogeneous solution, is stirred and heated to reflux under a flow of argon. After it is refluxed for a time sufficient to prepolymerize to form polyorganoalkoxysiloxane (POS), e.g., polyalkylalkoxysiloxane, the solvent and the side product, mainly ethanol, is distilled off from the reaction mixture. Thereafter, the residue is heated at an elevated temperature, e.g., in the range of 120 to 140° C. under an atmosphere of argon for a period of time, e.g., 1.5 to 16 h. The residue is further heated at this temperature, e.g., for 1 to 3 h under reduced pressure, e.g., 10$^{-2-10-3}$ torr, to remove any volatile species.

In the second step, the POS is suspended into fine beads in a solution containing water and ethanol at 55° C. by agitation. The volume percent of ethanol in the solution is varied from 10 to 20%. A non-ionic surfactant such as Triton X-100 or Triton X-45 is added into the suspension as the suspending agent. Alternatively a mixture of Triton X-45 and low levels of sodium dodecyl sulfate (SDS) or tris (hydroxymethyl)aminomethane lauryl sulfate (TDS) is added into the suspension as the suspending agent. The surfactants, e.g., alkylphenoxypolyethoxyethanol, are believed to be able to orient at the hydrophobic/hydrophilic interface between the POS beads and the aqueous phase to stabilize the POS beads. The surfactants are also believed to enhance the concentration of water and the base catalyst on the surface of the POS beads during the gelation step, through their hydrophilic groups, which induces the gelling of the POS beads from the surface towards the center. Use of surfactants to modulate the surface structure of the POS beads stabilizes the shape of the POS beads throughout the selling process, and minimizes or suppresses formation of particles having an irregular shapes, e.g., "shell shaped", and inhomogeneous morphology.

It is also possible to suspend a solution containing POS and toluene in the aqueous phase, instead of POS alone. The toluene, which is insoluble in the aqueous phase, remains in the POS beads during the gelation step and functions as a porogen. By controlling the relative amount of toluene in the POS/toluene solution, the pore volume of the final hybrid silica can be more precisely controlled. This allows the preparation of hybrid silica particles having large pore volume, e.g., 0.8–1.2 cm$^3$/g.

The gelation step is initiated by adding the basic catalyst, e.g., ammonium hydroxide into the POS suspension agitated at 55° C. Thereafter, the reaction mixture is agitated at the same temperature to drive the reaction to completion. Ammonium hydroxide is preferred because bases such as sodium hydroxide are a source of unwanted cations, and ammonium hydroxide is easier to remove in the washing step. The thus-prepared hybrid silica is filtered and washed with water and methanol free of ammonium ions, then dried.

In one embodiment, the pore structure of the as-prepared hybrid material is modified by hydrothermal treatment, which enlarges the openings of the pores as well as the pore diameters, as confirmed by nitrogen ($N_2$) sorption analysis. The hydrothermal treatment is performed by preparing a slurry containing the as-prepared hybrid material and a solution of organic base in water, heating the slurry in an autoclave at an elevated temperature, e.g., 143 to 168° C., for a period of 6 to 28 h. The pH of the slurry can be adjusted to be in the range of 8.0 to 10.7 using concentrated acetic acid. The concentration of the slurry is in the range of 1 g hybrid material per 5 to 10 ml of the base solution. The thus-treated hybrid material is filtered, and washed with water and acetone until the pH of the filtrate reaches 7, then dried at 100° C. under reduced pressure for 16 h. The resultant hybrid materials show average pore diameters in the range of 100–300 Å. The surface of the hydrothermally treated hybrid material may be modified in a similar fashion to that of the hybrid material that is not modified by hydrothermal treatment as described in the present invention.

The surface of the hydrothermally treated hybrid silica contains organic groups, which can be derivatized by reacting with a reagent that is reactive towards the particles' organic group. For example, vinyl groups on the particle can be reacted with a variety of olefin reactive reagents such as bromine ($Br_2$), hydrogen ($H_2$), free radicals, propagating polymer radical centers, dienes, and the like. In another example, hydroxyl groups on the particle can be reacted with a variety of alcohol reactive reagents such as isocyanates, carboxylic acids, carboxylic acid chlorides, and reactive organosilanes as described below. Reactions of this type are well known in the literature, see, e.g., March, J. "Advanced Organic Chemistry," 3$^{rd}$ Edition, Wiley, New York, 1985; Odian, G. "The Principles of Polymerization," 2$^{nd}$ Edition, Wiley, New York, 1981; the texts of which are incorporated herein by reference.

In addition, the surface of the hydrothermally treated hybrid silica also contains silanol groups, which can be derivatized by reacting with a reactive organosilane. The surface derivatization of the hybrid silica is conducted according to standard methods, for example by reaction with octadecyltrichlorosilane or octadecyldimethylchlorosilane in an organic solvent under reflux conditions. An organic solvent such as toluene is typically used for this reaction. An organic base such as pyridine or imidazole is added to the reaction mixture to catalyze the reaction. The product of this reaction is then washed with water, toluene and acetone and dried at 80° C. to 100° C. under reduced pressure for 16 h. The resultant hybrid silica can be further reacted with a short-chain silane such as trimethylchlorosilane to endcap the remaining silanol groups, by using a similar procedure described above.

More generally, the surface of the hybrid silica particles may be surface modified with a surface modifier, e.g., $Z_a(R')_b$Si—R, where Z=Cl, Br, I, $C_1$–$C_5$ alkoxy, dialkylamino, e.g., dimethylamino, or trifluoromethanesulfonate; a and b are each an integer from 0 to 3 provided that a+b=3; R' is a $C_1$–$C_6$ straight, cyclic or branched alkyl group, and R is a functionalizing group, and by coating with a polymer. R' may be, e.g., methyl, ethyl, propyl, isopropyl, butyl, t-butyl, sec-butyl, pentyl, isopentyl, hexyl or cyclohexyl; preferably, R' is methyl.

The functionalizing group R may include alkyl, alkenyl, alkynyl, aryl, cyano, amino, diol, nitro, cation or anion exchange groups, or alkyl or aryl groups with embedded polar functionalities. Examples of suitable R functionalizing groups include $C_1$–$C_{30}$ alkyl, including $C_1$–$C_{20}$, such as octyl ($C_8$), octadecyl ($C_{18}$), and triacontyl ($C_{30}$); alkaryl, e.g., $C_1$–$C_4$-phenyl; cyanoalkyl groups, e.g., cyanopropyl; diol groups, e.g., propyldiol; amino groups, e.g., aminopropyl; and alkyl or aryl groups with embedded polar functionalities, e.g., carbamate functionalities such as disclosed in U.S. Pat. No. 5,374,755, the text of which is incorporated herein by reference and as detailed hereinabove. In a preferred embodiment, the surface modifier may be an organotrihalosilane, such as octyltrichlorosilane or octadecyltrichlorosilane. In an additional preferred embodiment, the surface modifier may be a halopolyorganosilane, such as octyldimethylchlorosilane or octadecyldimethylchlorosilane. Advantageously, R is octyl or octadecyl.

Polymer coatings are known in the literature and may be provided generally by polymerization or polycondensation of physisorbed monomers onto the surface without chemical bonding of the polymer layer to the support (type I), polymerization or polycondensation of physisorbed monomers onto the surface with chemical bonding of the polymer layer to the support (type II), immobilization of physisorbed prepolymers to the support (type III), and chemisorption of presynthesized polymers onto the surface of the support (type IV), see, e.g., Hanson et al., *J. Chromat.* A656 (1993) 369–380, the text of which is incorporated herein by reference. As noted above, coating the hybrid material with a polymer may be used in conjunction with various surface modifications described in the invention.

The porous inorganic/organic hybrid particles have a wide variety of end uses in the separation sciences, such as packing materials for chromatographic columns (wherein such columns may have improved stability to alkaline mobile phases and reduced peak tailing for basic analytes), thin layer chromatographic (TLC) plates, filtration membranes, microtiter plates, scavenger resins, solid phase organic synthesis supports, and the like having a stationary phase which includes porous inorganic/organic hybrid particles having a chromatographically-enhancing pore geometry. The stationary phase may be introduced by packing, coating, impregnation, etc., depending on the requirements of the particular device. In a particularly advantageous embodiment, the chromatographic device is a packed chromatographic column, such as commonly used in HPLC.

EXAMPLES

The present invention may be further illustrated by the following non-limiting examples describing the preparation of porous inorganic/organic hybrid particles, and their use.

Example 1

An organoalkoxysilane and tetraethoxysilane (all from Gelest Inc., Tullytown, Pa.) are mixed with ethanol (HPLC grade, J. T. Baker, Phillipsburgh, N.J.) and 0.1 N hydrochloric acid (Aldrich Chemical, Milwaukee, Wis.) in a flask. The resulting solution is agitated and refluxed for 16 h in an atmosphere of argon or nitrogen. Ethanol and methanol (if applicable) are removed from the flask via distillation at atmospheric pressure. Residual alcohol and volatile species are removed by heating at 115–140° C. for 1–2 h in a sweeping stream of inert gas or by heating at 125° C. under reduced pressure for 1–2 h. The resulting polyorganoalkoxysiloxanes are colorless viscous liquids. The product numbers and the respective chemical formula of the organotrialkoxysilanes used in the copolymerization with tetraethoxysilane are listed in Table 1. The specific amounts of starting materials used to prepare these products are listed in Table 2.

TABLE 1

| Used in Products | Organoalkoxysilane Chemical Formula | Organic Group Name |
| --- | --- | --- |
| 1a, b, c | $CH_3Si(OCH_2CH_3)_3$ | methyl |
| 1d | $C_2H_5Si(OCH_2CH_3)_3$ | ethyl |
| 1e | $C_6H_5Si(OCH_2CH_3)_3$ | phenyl |
| 1f, g, h.i, j. | $(CH_3CH_2O)_3Si(CH_2)_2Si(OCH_2CH_3)_3$ | ethane bridge |
| 1k, l | $H_2C=CHSi(OCH_2CH_3)_3$ | vinyl |
| 1m, n, o | $H_2C=C(CH_3)CO_2C_3H_6Si(OCH_3)_3$ | methacryloxypropyl |
| 1p, q | $H_2C=CHC_6H_4C_2H_4Si(OCH_3)_3$ | styrylethyl |

TABLE 2

| Product | Mole Ratio: Organosilane/ TEOS | Organotri-alkoxysilane (g) | TEOS (g) | 0.1N HCl (g) | Ethanol (mL) |
| --- | --- | --- | --- | --- | --- |
| 1a | 0.20 | 137 | 802 | 109 | 400 |
| 1b | 0.35 | 249 | 832 | 116 | 300 |
| 1c | 0.50 | 534 | 1248 | 203 | 450 |
| 1d | 0.25 | 116 | 503 | 65 | 300 |
| 1e | 0.25 | 113 | 392 | 53 | 300 |
| 1f | 0.037 | 19 | 297 | 37 | 218 |
| 1g | 0.125 | 59 | 278 | 39 | 218 |
| 1h | 0.25 | 106 | 250 | 40 | 218 |
| 1i | 0.50 | 177 | 208 | 43 | 218 |
| 1j | 1.0 | 266 | 156 | 46 | 218 |
| 1k | 0.25 | 160 | 875 | 119 | 253 |
| 1l | 0.50 | 799 | 1750 | 297 | 736 |
| 1m | 0.10 | 179 | 1500 | 178 | 463 |
| 1n | 0.125 | 373 | 2500 | 304 | 788 |
| 1o | 0.25 | 671 | 2250 | 304 | 788 |
| 1p | 0.033 | 15 | 355 | 42 | 99 |
| 1q | 0.10 | 20 | 156 | 19 | 47 |

Example 2

A mixture of a surfactant (Triton X-45 or Triton X-100, Aldrich Chemical, Milwaukee, Wis.), ethanol (anhydrous, J. T. Baker, Phillipsburgh, N.J.), and deionized water was heated at 55° C. for 0.5 h, resulting in a white liquid. Under rapid agitation, a solution of toluene (HPLC grade, J. T. Baker, Phillipsburgh, N.J.) in polyorganalkoxysiloxane (selected from Table 2) was added into the ethanol/water/Triton mixture, and emulsified in the aqueous phase. Thereafter, 30% $NH_4OH$ (VWR, Bridgeport, N.J.) was added into the emulsion to gel the emulsion beads. Suspended in the solution, the gelled product was transferred to a flask and stirred at 55° C. for 16 h. The resulting spherical, porous, hybrid inorganic/organic particles were collected on 0.5 μm filtration paper and washed successively with water and methanol (HPLC grade, J. T. Baker, Phillipsburgh, N.J.). The products were then dried in a vacuum oven at 80° C. overnight. Specific amounts of starting materials used to prepare these products are listed in Table 3. $^{13}C$ and $^{29}Si$ CPMAS NMR spectra of the products are consistent with the assigned products with respect to organic group structure and ratio of organic/inorganic units. For products, 2q, 2r, and 2s, approximately 30% of the methacryoxypropyl ester groups were observed to hydrolyze to the corresponding 3-hydroxypropyl organic unit and methacrylic acid, where the acid was removed in the wash steps.

Example 3

A mixture of Triton X45 and sodium dodecylsulfate (SDS) (J. T. Baker, Phillipsburgh, N.J.) or tris(hydroxymethyl)aminomethane lauryl sulfate (TDS) (Fluka Chemical, Milwaukee, Wis.) was used to prepare spherical, porous, hybrid inorganic/organic particles made from the polyorganoalkoxysiloxanes consisting of bis(triethoxysilyl)ethane/TEOS molar ratios of 0.5 and 1.0 (Table 2, products 1i and 1j, respectively). The procedure was the same as described for Example 2, except that the 30% $NH_4OH$ was added to the emulsion after transfer from the emulsifier reactor to the stirred reaction flask. The molar ratio of Triton X-45/SDS or TDS was 1.2/1.0. Specific amounts of reagents used to prepare these products (2l, 2m, 2n) are listed in Table 3.

TABLE 3

| Product | Polyorgano-alkoxysilane Feedstock | Mole Ratio: Organosiloxane/$SiO_2$ in product | Polyorgano-alkoxysilane (g) | Toluene (mL) | Ethanol (mL) | Water (mL) | Surfactant Type | Surfactant (g) | Ammonium Hydroxide (mL) |
| --- | --- | --- | --- | --- | --- | --- | --- | --- | --- |
| 2a | 1a | 0.20 | 240 | 0 | 240 | 960 | X-100 | 20 | 150 |
| 2b | 1c | 0.50 | 240 | 0 | 240 | 960 | X-100 | 20 | 150 |
| 2c | 1a | 0.20 | 249 | 30 | 285 | 1200 | X-45 | 24 | 190 |
| 2d | 1b | 0.35 | 249 | 30 | 285 | 1200 | X-45 | 24 | 190 |
| 2e | 1c | 0.50 | 249 | 30 | 285 | 1200 | X-45 | 24 | 190 |

TABLE 3-continued

| Product | Polyorgano-alkoxysilane Feedstock | Mole Ratio: Organosiloxane/SiO$_2$ in product | Polyorgano-alkoxysilane (g) | Toluene (mL) | Ethanol (mL) | Water (mL) | Surfactant Type | Surfactant (g) | Ammonium Hydroxide (mL) |
|---|---|---|---|---|---|---|---|---|---|
| 2f | 1c | 0.50 | 249 | 60 | 285 | 1200 | X-45 | 24 | 190 |
| 2g | 1d | 0.25 | 240 | 0 | 240 | 960 | X-100 | 20 | 150 |
| 2h | 1e | 0.25 | 240 | 0 | 240 | 960 | X-100 | 20 | 150 |
| 2i | 1f | 0.037 | 58 | 7.0 | 66 | 280 | X-45 | 5.6 | 44 |
| 2j | 1g | 0.125 | 500 | 70 | 660 | 2800 | X-45 | 56 | 440 |
| 2k | 1h | 0.25 | 580 | 70 | 660 | 2800 | X-45 | 56 | 440 |
| 2l | 1i | 0.50 | 58 | 7.0 | 66 | 280 | X-45/SDS | 5.6 | 44 |
| 2m | 1i | 0.50 | 58 | 7.0 | 66 | 280 | X-45/TDS | 5.6 | 44 |
| 2n | 1j | 1.0 | 58 | 7.0 | 66 | 280 | X-45/SDS | 5.6 | 44 |
| 2o | 1k | 0.25 | 436 | 53 | 482 | 2100 | X-45 | 42 | 362 |
| 2p | 1l | 0.50 | 479 | 58 | 530 | 2310 | X-45 | 46 | 398 |
| 2q | 1m | 0.10 | 479 | 58 | 530 | 2310 | X-45 | 46 | 398 |
| 2r | 1n | 0.125 | 53 | 6.5 | 59 | 257 | X-45 | 5.2 | 44 |
| 2s | 1o | 0.25 | 53 | 6.5 | 59 | 257 | X-45 | 5.2 | 44 |
| 2t | 1p | 0.033 | 202 | 25 | 223 | 973 | X-45 | 19.5 | 168 |
| 2u | 1q | 0.10 | 53 | 6.6 | 59 | 257 | X-45 | 5.1 | 44 |

Example 4

Spherical, porous, hybrid inorganic/organic particles of Examples 2 were mixed with tris(hydroxymethyl)aminomethane (TRIS, Aldrich Chemical, Milwaukee, Wis.) in water, yielding a slurry. The pH of the slurry was adjusted as necessary to between 8 and 10.7 by adding concentrated acetic acid. The resultant slurry was then enclosed in a stainless steel autoclave and heated to between 140 and 165° C. for 20 h. After the autoclave cooled to room temperature the product was filtered and washed repeatedly using water and methanol (HPLC grade, J. T. Baker, Phillipsburgh, N.J.), and then dried at 80° C. under vacuum for 16 h. Specific hydrothermal conditions (mL of TRIS solution/gram of hybrid silica particle, concentration and pH of initial TRIS solution, reaction temperature) used to prepare these products are listed in Table 4. The specific surface areas (SSA), specific pore volumes (SPV) and the average pore diameters (APD) of these materials are measured using the multi-point $N_2$ sorption method and are listed in Table 5. The specific surface area was calculated using the BET method, the specific pore volume was the single point value determined for $P/P_0>0.99$, and the average pore diameter was calculated from the desorption leg of the isotherm using the BJH method. We also determined the micropore surface area (MPA), which we defined as the surface area in pores with diameters less than or equal to 34 Å, determined from the adsorption leg of the isotherm using the BJH method.

Methacryloxypropyl hybrid materials (e.g., 3q, 3r, 3s) were converted into 3-hydroxypropyl hybrid materials via hydrolysis of the ester bond during hydrothermal treatment. Conversion of the ester into the alcohol group was observed by a decrease in the % C of the particles before vs. after treatment. $^{13}$C CPMAS NMR spectra of the hydrothermally treated particles detect 3-hydroxypropyl groups only, however, FTIR spectra of the particles indicate the existence of a carbonyl containing group as evidenced by a weak band at 1695 cm$^{-1}$. Higher concentrations of TRIS solution were required to modify the pore structure of these particles because a portion of the base was sequestered as the methacrylic acid salt. The composition of methacryloxypropyl particles post hydrothermal treatment was relabeled to 3-hydroxypropyl. All post hydrothermal compositions were confirmed using % CHN, FTIR, $^{13}$C and $^{29}$Si CPMAS NMR spectroscopy.

TABLE 4

| | | | TRIS Conditions | | | |
|---|---|---|---|---|---|---|
| Product | Precursor | Prehydrothermal Composition of Hybrid Materials | Amount (mL/g) | Conc. (Molarity) | pH | Temp. (° C.) |
| 3a | 2a | SiO$_2$/(CH$_3$SiO$_{1.5}$)$_{0.2}$ | 10 | 0.10 | 8.0 | 143 |
| 3b | 2b | SiO$_2$/(CH$_3$SiO$_{1.5}$)$_{0.2}$ | 10 | 0.10 | 8.1 | 143 |
| 3c | 2c | SiO$_2$/(CH$_3$SiO$_{1.5}$)$_{0.2}$ | 10 | 0.10 | 8.4 | 155 |
| 3d | 2d | SiO$_2$/(CH$_3$SiO$_{1.5}$)$_{0.35}$ | 10 | 0.10 | 8.0 | 143 |
| 3e | 2e | SiO$_2$/(CH$_3$SiO$_{1.5}$)$_{0.5}$ | 10 | 0.10 | 8.3 | 143 |
| 3f1 | 2f1 | SiO$_2$/(CH$_3$SiO$_{1.5}$)$_{0.5}$ | 10 | 0.10 | 8.3 | 143 |
| 3f2 | 2f2 | SiO$_2$/(CH$_3$SiO$_{1.5}$)$_{0.5}$ | 10 | 0.10 | 8.75 | 148 |
| 3f3 | 2f3 | SiO$_2$/(CH$_3$SiO$_{1.5}$)$_{0.5}$ | 10 | 0.10 | 9.0 | 163 |
| 3g | 2g | SiO$_2$/(C$_2$H$_5$SiO$_{1.5}$)$_{0.25}$ | 10 | 0.10 | 8.3 | 143 |
| 3i | 2i | SiO$_2$/[C$_2$H$_4$(SiO$_{1.5}$)$_2$]$_{0.037}$ | 5 | 0.10 | 10.2 | 165 |
| 3j | 2j | SiO$_2$/[C$_2$H$_4$(SiO$_{1.5}$)$_2$]$_{0.125}$ | 5 | 0.10 | 10.0 | 165 |
| 3k | 2k | SiO$_2$/[C$_2$H$_4$(SiO$_{1.5}$)$_2$]$_{0.25}$ | 5 | 0.30 | 10.0 | 165 |
| 3l | 2l | SiO$_2$/[C$_2$H$_4$(SiO$_{1.5}$)$_2$]$_{0.5}$ | 5 | 0.30 | 10.2 | 165 |
| 3m | 2m | SiO$_2$/[C$_2$H$_4$(SiO$_{1.5}$)$_2$]$_{0.5}$ | 5 | 0.30 | 10.2 | 165 |
| 3n | 2n | SiO$_2$/[C$_2$H$_4$(SiO$_{1.5}$)$_2$]$_{1.0}$ | 5 | 0.30 | 10.2 | 165 |
| 3o | 2o | SiO$_2$/(H$_2$C=CHSiO$_{1.5}$)$_{0.25}$ | 5 | 0.10 | 8.5 | 155 |
| 3p1 | 2p | SiO$_2$/(H$_2$C=CHSiO$_{1.5}$)$_{0.5}$ | 5 | 0.10 | 8.5 | 155 |
| 3p2 | 2p | SiO$_2$/(H$_2$C=CHSiO$_{1.5}$)$_{0.5}$ | 5 | 0.10 | 10.2 | 155 |

TABLE 4-continued

| Product | Precursor | Prehydrothermal Composition of Hybrid Materials | TRIS Conditions | | | |
|---|---|---|---|---|---|---|
| | | | Amount (mL/g) | Conc. (Molarity) | pH | Temp. (° C.) |
| 3q | 2q | $SiO_2/[H_2C=C(CH_3)CO_2C_3H_6SiO_{1.5}]_{0.10}$ | 5 | 0.75 | 10.7 | 155 |
| 3r | 2r | $SiO_2/[H_2C=C(CH_3)CO_2C_3H_6SiO_{1.5}]_{0.125}$ | 5 | 0.75 | 10.7 | 155 |
| 3t | 2t | $SiO_2/(H_2C=CHC_6H_4C_2H_4SiO_{1.5})_{0.033}$ | 5 | 0.10 | 9.6 | 155 |
| 3u | 2u | $SiO_2/(H_2C=CHC_6H_4C_2H_4SiO_{1.5})_{0.10}$ | 5 | 0.75 | 10.7 | 155 |

TABLE 5

| Product | Post-hydrothermal Composition of Hybrid Materials | $N_2$ Sorption Data | | | |
|---|---|---|---|---|---|
| | | SSA ($m^2/g$) | SPV (cc/g) | APD (Å) | MPA ($m^2/g$) |
| 3a | $SiO_2/(CH_3SiO_{1.5})_{0.2}$ | 130 | 0.41 | 103 | 72 |
| 3b | $SiO_2/(CH_3SiO_{1.5})_{0.2}$ | 151 | 0.71 | 159 | 14 |
| 3c | $SiO_2/(CH_3SiO_{1.5})_{0.2}$ | 135 | 0.67 | 173 | 15 |
| 3d | $SiO_2/(CH_3SiO_{1.5})_{0.35}$ | 160 | 0.72 | 139 | 14 |
| 3e | $SiO_2/(CH_3SiO_{1.5})_{0.5}$ | 225 | 0.90 | 123 | 21 |
| 3f1 | $SiO_2/(CH_3SiO_{1.5})_{0.5}$ | 188 | 0.70 | 125 | 15 |
| 3f2 | $SiO_2/(CH_3SiO_{1.5})_{0.5}$ | 155 | 0.69 | 148 | 15 |
| 3f3 | $SiO_2/(CH_3SiO_{1.5})_{0.5}$ | 125 | 0.62 | 168 | 13 |
| 3g | $SiO_2/(C_2H_5SiO_{1.5})_{0.25}$ | 267 | 0.94 | 139 | 53 |
| 3i | $SiO_2/[C_2H_4(SiO_{1.5})_2]_{0.037}$ | 162 | 0.52 | 122 | 28 |
| 3j | $SiO_2/[C_2H_4(SiO_{1.5})_2]_{0.125}$ | 127 | 0.81 | 238 | 31 |
| 3k | $SiO_2/[C_2H_4(SiO_{1.5})_2]_{0.25}$ | 162 | 0.52 | 122 | 28 |
| 3l | $SiO_2/[C_2H_4(SiO_{1.5})_2]_{0.5}$ | 122 | 0.48 | 133 | 23 |
| 3m | $SiO_2/[C_2H_4(SiO_{1.5})_2]_{0.5}$ | 155 | 0.45 | 101 | 34 |
| 3n | $SiO_2/[C_2H_4(SiO_{1.5})_2]_{1.0}$ | 150 | 0.45 | 107 | 32 |
| 3o | $SiO_2/(H_2C=CHSiO_{1.5})_{0.25}$ | 143 | 0.73 | 194 | 26 |
| 3p1 | $SiO_2/(H_2C=CHSiO_{1.5})_{0.5}$ | 219 | 0.65 | 141 | 101 |
| 3p2 | $SiO_2/(H_2C=CHSiO_{1.5})_{0.5}$ | 165 | 0.54 | 155 | 94 |
| 3q | $SiO2/[HOC_3H_6SiO_{1.5}]_{0.10}$ | 324 | 1.04 | 113 | 23 |
| 3r | $SiO_2/[HOC_3H_6SiO_{1.5}]_{0.125}$ | 353 | 0.76 | 79 | 50 |
| 3t | $SiO_2/(H_2C=CHC_6H_4C_2H_4SiO_{1.5})_{0.033}$ | 153 | 0.62 | 153 | 31 |
| 3u | $SiO_2/(H_2C=CHC_6H_4C_2H_4SiO_{1.5})_{0.10}$ | 193 | 0.55 | 102 | 58 |

Example 5

The particles of hybrid silica prepared according to Example 5 were separated by particle size into ~3, ~5, and ~7 μm fractions. The particles were then dispersed in a 1 molar hydrochloric acid solution (Aldrich Chemical) for 20 h at 98° C. After the acid treatment was completed, the particles were washed with water to a neutral pH, followed by acetone (HPLC grade, J. T. Baker, Phillipsburgh, N.J.). The particles were then dried at 80° C. under vacuum for 16 h.

Example 6

Vinyl hybrid silica particles (product 3p1 of Example 5) were sized and acid washed according to Example 5. A 20 g amount of the 5 μm vinyl hybrid particles were added onto an 80 mm OD watch glass and placed inside a 90×170 mm (H×OD) crystallizing dish. Fuming bromine, 5 mL (Aldrich Chemical), was then added around the outside diameter of the watch glass, and the crystallization dish was covered with an inverted 100×190 mm (H×OD) crystallization dish. The bromination reaction was performed at ambient temperature for 18 h. Excess bromine was subsequently removed, and the material was washed exhaustively with methylene chloride (HPLC grade, J. T. Baker), water, and again with methylene chloride. The brominated particles were then dried at 80° C. under vacuum for 16 h. Incorporation of 18.6% bromine was measured by combustion-titration analysis (Galbraith Laboratories, Knoxville, Tenn.), and 20% of the vinyl groups were converted into the dibromoethane analog as determined by $^{13}C$ CPMAS NMR spectroscopy.

Example 7

Vinyl hybrid silica particles (product 3p1 of Example 5) were sized and acid washed according to Example 5. A 50 g amount of the 5 μm vinyl hybrid particles was combined with 15.0 g p-toluenesulfonhydrazide (Aldrich Chemical), 14.3 g tripropylamine (Aldrich Chemical), and 300 mL o-xylene (Aldrich Chemical) in a 500 mL three-neck round-bottom flask. The reaction mixture was heated to 140° C. for 6 h, and was then cooled to room temperature (30° C.). The flask was recharged with the same amount of p-toluenesulfonhydrazide and tripropylamine, and the reaction mixture was reheated to 140° C. for another 16 h. The particles were then washed exhaustively with toluene, acetone, acetone/water (50/50, v/v), and acetone (all solvents HPLC grade, J. T. Baker). The washed particles were then dried at 80° C. under vacuum for 16 h. The dried particles were reacted an additional 7 successive times, as described above, to afford a 1/20 ratio of unreacted vinyl groups to hydrogenated vinyl groups (i.e., ethyl). The vinyl content was found to decrease with each successive reaction as measured by $^{13}C$ CPMAS NMR spectroscopy.

Example 8

Vinyl hybrid silica particles (product 3p1 of Example 5) were sized and acid washed according to Example 5. A 10 g amount of the 5 μm vinyl hybrid particles was combined with 62 g of 4,4'-azobis(4-cyanovaleric acid) (Aldrich Chemical) in 125 mL of a methanol/water (50/50, v/v) solution. The suspension was deoxygenated by bubbling argon gas through it for 1 h, after which an argon blanket was maintained over the suspension. The suspension was then heated to 70° C. for 20 h and subsequently cooled to room temperature. The mixture was transferred to a filter apparatus and washed exhaustively with toluene, acetone/water (50/50, v/v), and acetone (all solvents HPLC grade, J. T. Baker). The washed particles were then dried at 80° C. under vacuum for 16 h. Coupling of 4-cyanovaleric acid to the vinyl group of the skeletal structure through a covalent organic bond was established by an 18% increase in particle carbon content, and an ion-exchange capacity of 0.18 meq/g assigned to the carboxylic group.

Example 9

Vinyl hybrid silica particles (product 3p1 of Example 5) were sized and acid washed according to Example 5. A 10 g amount of the 5 μm vinyl hybrid particles was combined with 62 g of 2,2'-azobis(2-methylpropionamidine) dihydrochloride (Aldrich Chemical) in 125 mL of a methanol/water (50/50, v/v) solution. The suspension was deoxygenated by bubbling argon gas through it for 1 h, after which an argon blanket was maintained over the suspension. The suspension was heated to 50° C. for 20 h and subsequently cooled to room temperature. The mixture was transferred to a filter apparatus and washed exhaustively with toluene, acetone/water (50/50, v/v), and acetone (all solvents HPLC grade, J. T. Baker). The washed particles were then dried at 80° C. under vacuum for 16 h. Coupling of (2-methylpropionamidine) hydrochloride to the vinyl group of the skeletal structure through a covalent organic bond was established by a 10% increase in particle carbon content, and an ion-exchange capacity of 0.15 meq/g, assigned to the amidine hydrochloride group. Furthermore, $^{13}$C CPMAS NMR spectroscopy of the particles showed resonances assigned to the 2-methylpropionamidine group.

Example 10

Vinyl hybrid silica particles (product 3p1 of Example 5) were sized and acid washed according to Example 5. A 2 g amount of the 7 μm vinyl hybrid particles was combined with 2.1 g of N-octadecylacrylamide (Aldrich Chemical) in 20 mL of toluene (J. T. Baker). The suspension was deoxygenated by bubbling argon gas through it for 1 h, after which an argon blanket was maintained over the suspension. While maintaining an argon blanket, 0.4 g of VAZO 88 was added to the reaction, and the reaction mixture was heated to 70° C. for 17 h. The flask was then cooled to room temperature, and the particles were transferred to a filter apparatus. The filtered particles were washed exhaustively with tetrahydrofuran, toluene, acetone, acetone/water (50/50, v/v), and acetone (all solvents HPLC grade, J. T. Baker). The washed particles were then dried at 80° C. under vacuum for 16 h. Radical initiated coupling of octadecylacrylamide groups with vinyl groups of the skeletal structure through a covalent organic bond was established by a 29% increase in particle carbon content, which converts to a surface concentration of 1.02 μmol/m$^2$. Furthermore, $^{13}$C CPMAS NMR and FTIR spectroscopy of the particles showed resonances consistent with octadecylacrylamide addition to the vinyl groups.

Example 11

Vinyl hybrid silica particles (product 3p1 of Example 5) were sized and acid washed according to Example 5. A 3 g amount of the 7 μm vinyl hybrid particles was combined with 0.9 g dicyclopentadiene (Aldrich Chemical) in 25 mL of toluene (J. T. Baker). The suspension was heated to reflux (111° C.) for 16 h and then cooled to room temperature. The particles were transferred to a filter apparatus and washed exhaustively with toluene and acetone (both HPLC grade, J. T. Baker). The washed particles were then dried at 80° C. under vacuum for 16 h. Diels-Alder cycloaddition of cyclopentadiene with the vinyl groups through a covalent organic bond was established by a 14% increase in particle carbon content that is analogous to a surface concentration of 1.36 μmol/m$^2$. Furthermore, $^{13}$C CPMAS NMR and FTIR spectroscopy of the particles showed resonances consistent with diene addition.

Example 12

Propanol hybrid silica particles (product 3q of Example 5) were sized and acid washed according to Example 5. A 3 g amount of the dried 6 μm propanol hybrid particles and 4.9 g of octylisocyanate (Aldrich Chemical) were combined with 75 mL of dry toluene (J. T. Baker) under an argon blanket. The suspension was heated to reflux (111° C.) for 4 h and then cooled to 60° C. The particles were transferred to a filter apparatus and washed exhaustively with toluene heated to 80° C. and then room temperature acetone (both HPLC grade, J. T. Baker). The washed particles were then dried at 80° C. under vacuum for 16 h. Reaction of the octyl isocyanate molecule with the hybrid particle's hydroxyl group to form a carbamate group and thereby connect the octyl chain to the particle's skeletal structure through a covalent organic bond was established by a 94% increase in particle carbon content that is analogous to a surface concentration of 1.59 μmol/m$^2$ of O-propylsilyl N-octyl carbamate group. Furthermore, $^{13}$C CPMAS NMR spectroscopy of the particles showed resonances consistent with addition product, where 40% of the propanol groups were converted to carbamate groups, and the remaining propanol groups remained unreacted.

Example 13

A 3 g amount of the dried 6 μm propanol hybrid particles, as described in Example 12, and 6.7 g of dodecyl isocyanate (Aldrich Chemical) were combined with 75 mL of dry toluene (J. T. Baker) and reacted in the same way as described in Example 12. Addition of the dodecyl isocyanate molecule to the hybrid particle's hydroxyl group to form a carbamate group and thereby connect the dodecyl chain to the particle's skeletal structure through a covalent organic bond was established by the reaction procedure and a 119% increase in particle carbon content that is analogous to a surface loading of 1.41 μmol/m$^2$ of O-propylsilyl N-dodecyl carbamate group. Furthermore, $^{13}$C CPMAS NMR spectroscopy of the particles showed resonances consistent with addition product, where 40% of the propanol groups were converted to carbamate groups, and the remaining propanol groups remained unreacted.

Example 14

Propanol hybrid silica particles (product 3q of Example 5) were sized and acid washed according to Example 5. A 3 g amount of the dried 6 μm propanol hybrid particles, 0.47 g of p-toluenesulfonic acid (Aldrich Chemical), and 10.0 g of lauric acid (Sigma Chemical, St. Louis, Mo.) were combined with 100 mL of dry xylene (J. T. Baker) under an argon blanket. The suspension was heated to reflux (145° C.) for 16 h and then cooled to 30° C. The particles were then transferred to a filter apparatus and washed exhaustively with toluene, acetone, acetone/water (50/50, v/v), and acetone again (all solvents HPLC grade, J. T. Baker). The washed particles were then dried at 80° C. under vacuum for 16 h. Reaction of the lauric acid molecule with the hybrid particle's hydroxyl group to form a carboxylic acid ester bond and thereby connect the n-$C_{11}H_{23}$ alkyl chain to the particle's skeletal structure through a covalent organic bond was established by the reaction procedure and a 157% increase in particle carbon content, which converts to a surface concentration of 2.06 μmol/m$^2$ of n-$C_{11}H_{23}$ alkyl groups. Furthermore, $^{13}$C CPMAS NMR spectroscopy of the particles showed resonances consistent with ester product, where 30% of the propanol groups were converted to ester groups, and the remaining propanol groups remained unreacted.

Example 15

Propanol hybrid silica particles (product 3q of Example 5) were sized and acid washed according to Example 5. A 3 g amount of the dried 6 μm propanol hybrid particles and 3.3 mL of dried triethylamine (Aldrich Chemical) were combined with 150 mL of dry dichloromethane (HPLC grade, J. T. Baker) under an argon blanket and chilled to 5° C. Maintaining a temperature of 5° C., 1.95 mL of methacryloyl chloride (Aldrich Chemical) was added dropwise to the suspension. Three additional aliquots of triethylamine and methacryloyl chloride were added for a combined total of 13.2 mL triethylamine and 7.8 mL methacryloyl chloride. The suspension was allowed to warm to room temperature and was stirred an additional 16 h. The particles were transferred to a filter apparatus and washed exhaustively with dichloromethane, acetone, water, and again with acetone (all solvents HPLC grade, J. T. Baker). The washed particles were then dried at 80° C. under vacuum for 16 h. Reaction of the methacryloyl chloride molecule with the hybrid particle's hydroxyl group to form a carboxylic acid ester bond and thereby connect the methacrylate's vinyl group to the particle's skeletal structure through a covalent organic bond was established by a 63% increase in particle carbon content that is analogous to a surface concentration of 2.30 μmol/m$^2$ of methacrylate groups. Furthermore, $^{13}$C CPMAS NMR spectroscopy of the particles showed resonances consistent with ester product, where 60% of the propanol groups were converted to ester groups, and the remaining propanol groups remained unreacted.

Example 16

A 0.5 g amount of the dried styrylethyl hybrid particles (product 3t of Example 5) was brominated in the manner described in Example 6. Greater than 99% of the vinyl groups were converted into the dibromoethane analog as determined by $^{13}$C CPMAS NMR spectroscopy.

Example 17

Styrylethyl hybrid silica particles (product 3u of Example 5) were sized according to Example 5. A 0.5 g amount of the dried 8 μm styrylethyl hybrid particles was brominated in the manner described in Example 6. Greater than 99% of the vinyl groups were converted into the dibromoethane analog as determined by $^{13}$C CPMAS NMR spectroscopy.

Example 18

A 2.0 g amount of the dried styrylethyl hybrid particles (product 3t of Example 5) was suspended in 20 mL of toluene (J. T. Baker) and refluxed for 2 h under an argon atmosphere to deoxygenate and removed adsorbed water via azeotrope. After cooling to room temperature under dry argon, 0.6 g of 1,1'-azobis(cyclohexanecarbonitrile) (Aldrich Chemical) was added. The suspension was stirred and heated to 80° C. for 17 h then heated to 100° C. for 2.5 h. After cooling, the particles were recovered by filtration, and exhaustively washed with toluene, dichloromethane and acetone. The washed particles were then dried at 80° C. under vacuum for 16 h. Reaction of the cyclohexanecarbonitrile molecule with the hybrid particle's vinyl group, thereby connecting the reagent to the particle's skeletal structure through a covalent organic bond was established by a 23% increase in particle carbon content that is analogous to a surface concentration of 1.09 μmol/m$^2$ of cyclohexanecarbonitrile groups. Greater than 99% of the vinyl groups were polymerized as determined by $^{13}$C CPMAS NMR spectroscopy.

Example 19

Styrylethyl hybrid silica particles (product 3u of Example 5) were sized according to Example 5. A 2.0 g amount of the dried 8 μm styrylethyl hybrid particles was reacted with 0.9 g of 1,1'-azobis(cyclohexanecarbonitrile) in the manner described above for Example 18. Reaction of the cyclohexanecarbonitrile molecule with the hybrid particle's vinyl group, thereby connecting the reagent to the particle's skeletal structure through a covalent organic bond was established by a 9.7% increase in particle carbon content, which converts to a surface concentration of 1.07 μmol/m$^2$ of cyclohexanecarbonitrile groups. Greater than 99% of the vinyl groups were polymerized as determined by $^{13}$C CPMAS NMR spectroscopy.

Example 20

A 2.0 g amount of the dried styrylethyl hybrid particles (product 3t of Example 5) was combined with 0.29 g of 1,1'-azobis(cyclohexanecarbonitrile) (Aldrich Chemical) and 25 mL of dichloromethane (J. T. Baker) in a 25 mL round-bottom flask. After stirring the suspension until the radical initiator was dissolved, the dichloromethane was removed from the suspension by rotary-evaporation. The initiator coated particles were dried under high vacuum (0.1 mm Hg) for 18 h. In a similar sized flask, 10 mL of styrene (Aldrich Chemical) was added and degassed via high vacuum. Under a closed, reduced pressure system, styrene vapor was allowed to equilibrate between the two flasks for 1.5 h, thereby adsorbing onto the styrylethyl hybrid particles. The coated, styrylethyl hybrid particles were then vented to argon and heated to 80° C. for 20 h. After cooling, the particles were recovered by filtration and exhaustively washed with toluene, dichloromethane and acetone. The washed particles were then dried at 80° C. under vacuum for 16 h. Greater than 99% of the vinyl groups were copolymerized with the adsorbed styrene as determined by $^{13}$C CPMAS NMR spectroscopy. Reaction of the cyclohexanecarbonitrile and styrene molecules with the hybrid particle's vinyl group thereby connecting the reagents to the particle's skeletal structure through a covalent organic bond was established by a 16.3% increase in particle carbon content.

Example 21

Styrylethyl hybrid silica particles (product 3u of Example 5) were sized according to Example 5. A 2.0 g amount of the dried 8 μm styrylethyl hybrid particles was reacted with 0.25 g of 1,1'-azobis(cyclohexanecarbonitrile) in the manner described above for Example 20. Greater than 99% of the vinyl groups were copolymerized with the adsorbed styrene as determined by $^{13}$C CPMAS NMR spectroscopy. Reaction of the cyclohexanecarbonitrile and styrene molecules with the hybrid particle's vinyl group, thereby connecting the reagents to the particle's skeletal structure through a covalent organic bond was established by a 42% increase in particle carbon content.

Example 22

Styrylethyl hybrid silica particles (product 3u of Example 5) were sized according to Example 5. A 2.0 g amount of the dried 8 μm styrylethyl hybrid particles was reacted with 0.20 g of 1,1'-azobis(cyclohexanecarbonitrile) in the manner described above for Example 20, with the exception that divinylbenzene (Aldrich Chemical) was used as the adsorbed monomer. Greater than 99% of the vinyl groups were copolymerized with the adsorbed divinylbenzene as determined by $^{13}$C CPMAS NMR spectroscopy. Reaction of the cyclohexanecarbonitrile and divinylbenzene molecules with the hybrid particle's vinyl group, thereby connecting the reagents to the particle's skeletal structure through a covalent organic bond was established by a 37% increase in particle carbon content.

Example 23

The surfaces of the hybrid silica particles were modified with a variety of chlorotrialkylsilanes as follows: $1 \times 10^{-5}$ moles of silane per square meter of particle surface area and 1.2 equivalents (per mole silane) of a base activator such as 4-(dimethylamino)pyridine (Aldrich Chemical), imidazole (Aldrich Chemical), or pyridine (J. T. Baker) were added to a mixture of 10 g of hybrid silica in 50 mL of toluene (J. T. Baker), and the resultant mixture was refluxed for 2–4 h. The modified hybrid silica particles were filtered and washed successively with water, toluene, 1:1 v/v acetone/water, and acetone (all solvents from J. T. Baker), and then dried at 80° C. under reduced pressure for 16 h. The surface concentration ($\mu mol/m^2$) of trialkylsilyl groups was determined by the difference in particle % C before and after the surface modification as measured by elemental analysis.

A secondary surface modification or end capping reaction was performed using a second silane, chlorotrimethylsilane (Aldrich Chemical), following the above procedure with respect to reagent amounts and reaction conditions. Table 6 lists the unmodified hybrid particle composition, the chemical formula of the first silane, the chemical formula of the second or end capping silane, the surface concentration of the first silane bonded phase, and total % C for selected final modified particles. Silanes and their sources were as follows: chlorodimethyloctadecylsilane and chlorotrimethylsilane (both from Aldrich Chemical); 3-(chlorodimethylsilyl)propyl N-octadecylcarbamate, 3-(chlorodimethylsilyl)propyl N-dodecylcarbamate, and 3-(chlorodimethylsilyl)propyl N-benzylcarbamate (all prepared as described in Neue, Niederländer, and Petersen in U.S. Pat. No. 5,374,755); [3-(pentafluorophenyl)-propyl]dimethylchlorosilane, octyldiisopropylchlorosilane, and triacontyldimethylchlorosilane (all from Gelest, Inc.).

TABLE 6

| Product | Composition of Hybrid Material Prior to Modification | Primary Silane Chemical Formula | Secondary Silane Chemical Formula | Surface Concentration ($\mu mol/m^2$) | % C Final Modified Particle |
|---|---|---|---|---|---|
| 24a | $SiO_2/(CH_3SiO_{1.5})_{0.2}$ | $CH_3(CH_2)_{17}Si(CH_3)_2Cl$ | $ClSi(CH_3)_3$ | 2.73 | 11.06 |
| 24b | $SiO_2/(CH_3SiO_{1.5})_{0.35}$ | $CH_3(CH_2)_{17}Si(CH_3)_2Cl$ | $ClSi(CH_3)_3$ | 2.50 | 14.80 |
| 24c | $SiO_2/(CH_3SiO_{1.5})_{0.5}$ | $CH_3(CH_2)_{17}Si(CH_3)_2Cl$ | $ClSi(CH_3)_3$ | 2.18 | 15.02 |
| 24d | $SiO_2/(CH_3SiO_{1.5})_{0.5}$ | $CH_3(CH_2)_{17}Si(CH_3)_2Cl$ | $ClSi(CH_3)_3$ | 2.23 | 17.21 |
| 24e | $SiO_2/(CH_3SiO_{1.5})_{0.5}$ | $CH_3(CH_2)_{17}NHC(O)O(CH_2)_3Si(CH_3)_2Cl$ | $ClSi(CH_3)_3$ | 1.80 | 14.84 |
| 24f | $SiO_2/(CH_3SiO_{1.5})_{0.5}$ | $CH_3(CH_2)_{11}NHC(O)O(CH_2)_3Si(CH_3)_2Cl$ | $ClSi(CH_3)_3$ | 2.34 | 14.74 |
| 24g | $SiO_2/(CH_3SiO_{1.5})_{0.5}$ | $CH_3(CH_2)_7NHC(O)O(CH_2)_3Si(CH_3)_2Cl$ | $ClSi(CH_3)_3$ | 2.42 | 13.46 |
| 24h | $SiO_2/(CH_3SiO_{1.5})_{0.5}$ | $C_6H_5(CH_2)NHC(O)O(CH_2)_3Si(CH_3)_2Cl$ | $ClSi(CH_3)_3$ | 2.49 | 13.02 |
| 24i | $SiO_2/(CH_3SiO_{1.5})_{0.5}$ | $C_6F_5(CH_2)_3Si(CH_3)_2Cl$ | $ClSi(CH_3)_3$ | 2.27 | 11.66 |
| 24j | $SiO_2/(CH_3SiO_{1.5})_{0.5}$ | $CH_3(CH_2)_7Si[CH(CH_3)_2]_2Cl$ | $ClSi(CH_3)_3$ | 1.23 | 10.76 |
| 24k | $SiO_2/(CH_3SiO_{1.5})_{0.5}$ | $CH_3(CH_2)_{29}Si(CH_3)_2Cl$ | $ClSi(CH_3)_3$ | 1.94 | 18.48 |
| 24l | $SiO_2/[C_2H_4(SiO_{1.5})_2]_{0.25}$ | $CH_3(CH_2)_{11}NHC(O)O(CH_2)_3Si(CH_3)_2Cl$ | $ClSi(CH_3)_3$ | 2.55 | 15.28 |
| 24m | $SiO_2/[HOC_3H_6SiO_{1.5}]_{0.10}$ | $CH_3(CH_2)_7Si[CH(CH_3)_2]_2Cl$ | — | 1.74 | 13.89 |
| 24n | $SiO_2/[RSiO_{1.5}]_{0.10}$ where R = 60% $HOC_3H_6$ and 40% $CH_3(CH_2)_7NHC(O)OC_3H_6$ | $ClSi(CH_3)_3$ | — | 2.44 | 12.95 |
| 24o | $SiO_2/[RSiO_{1.5}]_{0.10}$ where R = 60% $HOC_3H_6$ and 40% $CH_3(CH_2)_{11}NHC(O)OC_3H_6$ | $ClSi(CH_3)_3$ | — | 3.10 | 14.50 |

Example 24

The surfaces of the hybrid silica particles were modified with a variety of dialkyldichlorosilanes, alkyltrichlorosilanes, and alkyltrialkoxysilanes as follows: $1 \times 10^{-5}$ moles of silane per square meter of particle surface area and 1.2 equivalents (per mole silane) of a base activator such as 4-(dimethylamino)pyridine (Aldrich Chemical), imidazole (Aldrich Chemical), or pyridine (J. T. Baker) were added to a mixture of 10 g of hybrid silica in 50 mL of toluene (J. T. Baker) and the resultant mixture was refluxed for 2–4 h. The modified hybrid silica particles were filtered and washed successively with toluene, 1:1 v/v acetone/water, and acetone (all solvents from J. T. Baker). The washed particles were then heated in a 4.5:1 v/v solution of acetone/0.12 M ammonium acetate for 2.0–3.0 hours at 60° C. The particles were subsequently cooled, filtered, and washed successively propyl)trichlorosilane, (3-phenylpropyl)methyldichlorosilane, (4-phenylbutyl)methyldichlorosilane, phenethyltrichlorosilane, [3-(pentafluorophenyl)propyl]trichlorosilane, triacontyltrichlorosilane (all from Silar Laboratories, Scotia, N.Y.); (2-phenylpropyl)methyldichlorosilane (Gelest Inc.); 1H,1H,2H,2H-perfluorooctyltriethoxysilane (Sivento, Piscataway, N.J.); phenyltrichlorosilane, 3-cyanopropyltrichlorosilane (Hüls, Piscataway, N.J.).

TABLE 7

| Product | Composition Hybrid Material Prior to Modification | Primary Silane Chemical Formula | Secondary Silane Chemical Formula | Surface Concentration ($\mu mol/m^2$) | % C Final Modified Particle |
|---|---|---|---|---|---|
| 25a | $SiO_2/(CH_3SiO_{1.5})_{0.5}$ | $CH_3(CH_2)_{17}Si(CH_3)Cl_2$ | $ClSi(CH_3)_3$ | 2.23 | 15.31 |
| 25b | $SiO_2/(CH_3SiO_{1.5})_{0.5}$ | $C_6H_5(CH_2)_3Si(CH_3)Cl_2$ | $ClSi(CH_3)_3$ | 2.31 | 12.25 |
| 25c | $SiO_2/(CH_3SiO_{1.5})_{0.5}$ | $C_6H_5(CH_2)_3Si(CH_3)Cl_2$ | $ClSi(CH_2CH_3)_3$ | 2.31 | 12.39 |
| 25d | $SiO_2/(CH_3SiO_{1.5})_{0.5}$ | $C_6H_5(CH_2)_3Si(CH_3)Cl_2$ | $Cl(CH_3)_2SiC(CH_3)_3$ | 2.31 | 12.07 |
| 25e | $SiO_2/(CH_3SiO_{1.5})_{0.5}$ | $C_6H_5(CH_3)CHCH_2Si(CH_3)Cl_2$ | $ClSi(CH_3)_3$ | 2.11 | 11.76 |
| 25f | $SiO_2/(CH_3SiO_{1.5})_{0.5}$ | $C_6H_5(CH_2)_4Si(CH_3)Cl_2$ | $ClSi(CH_3)_3$ | 2.37 | 12.76 |
| 25g | $SiO_2/(CH_3SiO_{1.5})_{0.5}$ | $CH_3(CH_2)_{29}SiCl_3$ | $ClSi(CH_3)_3$ | 2.30 | 19.84 |
| 25h | $SiO_2/(CH_3SiO_{1.5})_{0.5}$ | $CH_3(CH_2)_{17}SiCl_3$ | $ClSi(CH_3)_3$ | 2.13 | 15.43 |
| 25i | $SiO_2/(CH_3SiO_{1.5})_{0.5}$ | $CH_3(CH_2)_{17}SiCl_3$ | $ClSi(CH_2CH_3)_3$ | 2.13 | 15.75 |
| 25j | $SiO_2/(CH_3SiO_{1.5})_{0.5}$ | $CH_3(CH_2)_{17}SiCl_3$ | $Cl(CH_3)_2SiC(CH_3)_3$ | 2.13 | 15.33 |
| 25k | $SiO_2/(CH_3SiO_{1.5})_{0.5}$ | $CH_3(CH_2)_7SiCl_3$ | $ClSi(CH_3)_3$ | 2.23 | 11.70 |
| 25l | $SiO_2/(CH_3SiO_{1.5})_{0.5}$ | $CF_3(CF_2)_5(CH_2)_2Si(OCH_2CH_3)_3$ | $ClSi(CH_3)_3$ | 1.46 | 9.90 |
| 25m | $SiO_2/(CH_3SiO_{1.5})_{0.5}$ | $C_6F_5(CH_2)_3SiCl_3$ | $ClSi(CH_3)_3$ | 2.13 | 11.67 |
| 25n | $SiO_2/(CH_3SiO_{1.5})_{0.5}$ | $C_6H_5(CH_2)_2SiCl_3$ | $ClSi(CH_3)_3$ | 2.42 | 12.02 |
| 25o | $SiO_2/(CH_3SiO_{1.5})_{0.5}$ | $C_6H_5(CH_2)_2SiCl_3$ | $ClSi(CH_2CH_3)_3$ | 2.35 | 12.09 |
| 25p | $SiO_2/(CH_3SiO_{1.5})_{0.5}$ | $C_6H_5(CH_2)_2SiCl_3$ | $Cl(CH_3)_2SiC(CH_3)_3$ | 2.42 | 11.72 |
| 25q | $SiO_2/(CH_3SiO_{1.5})_{0.5}$ | $C_6H_5(CH_2)_4SiCl_3$ | $ClSi(CH_3)_3$ | 2.20 | 12.57 |
| 25r | $SiO_2/(CH_3SiO_{1.5})_{0.5}$ | $C_6H_5SiCl_3$ | $ClSi(CH_3)_3$ | 2.09 | 10.74 |
| 25s | $SiO_2/(CH_3SiO_{1.5})_{0.5}$ | $C_6H_5SiCl_3$ | $Cl(CH_3)_2SiC(CH_3)_3$ | 2.09 | 10.88 |
| 25t | $SiO_2/(CH_3SiO_{1.5})_{0.5}$ | $NC(CH_2)_3SiCl_3$ | — | 2.31 | — |
| 25u | $SiO_2/[C_2H_4(SiO_{1.5})_2]_{0.25}$ | $CH_3(CH_2)_{17}SiCl_3$ | $ClSi(CH_3)_3$ | 2.62 | 15.74 |
| 25v | $SiO_2/(H_2C=CHSiO_{1.5})_{0.5}$ | $CH_3(CH_2)_{17}SiCl_3$ | $ClSi(CH_3)_3$ | 1.28 | 18.26 |
| 25w | $SiO_2/(RSiO_{1.5})_{0.5}$ where R = 20% $BrCH_2CHBr$ and 80% $H_2C=CH$ | $CH_3(CH_2)_{17}SiCl_3$ | $ClSi(CH_3)_3$ | 1.73 | 14.31 |
| 25x | $SiO_2/(RSiO_{1.5})_{0.5}$ where R = 95% $CH_3CH_2$ and 5% $H_2C=CH$ | $CH_3(CH_2)_{17}SiCl_3$ | $ClSi(CH_3)_3$ | 1.38 | 17.14 |
| 25y | $SiO_2/(RSiO_{1.5})_{0.5}$ where R = 3.4% $HO_2CCH_2CH_2C(CH_3)(CN)-CH_2CH_2$ and 96.6% $H_2C=CH$ | $CH_3(CH_2)_{17}SiCl_3$ | $ClSi(CH_3)_3$ | 0.86 | 18.29 |
| 25z | $SiO_2/(RSiO_{1.5})_{0.5}$ where R = 3.4% $HCl.H_2N(HN=)C(CH_3)_2-CH_2CH_2$ and 96.6% $H_2C=CH$ | $CH_3(CH_2)_{17}SiCl_3$ | $ClSi(CH_3)_3$ | 1.23 | 18.85 |
| 25aa | $SiO_2/[HOC_3H_6SiO_{1.5}]_{0.10}$ | $CH_3(CH_2)_{29}SiCl_3$ | $ClSi(CH_3)_3$ | 2.16 | 19.03 |
| 25bb | $SiO_2/[HOC_3H_6SiO_{1.5}]_{0.10}$ | $CH_3(CH_2)_{17}SiCl_3$ | $ClSi(CH_3)_3$ | 2.30 | 25.47 |
| 25cc | $SiO_2/[HOC_3H_6SiO_{1.5}]_{0.10}$ | $C_6F_5(CH_2)_3SiCl_3$ | $ClSi(CH_3)_3$ | 1.92 | 13.01 | with 1:1 v/v acetone/water, and acetone, and then dried at 80° C. under reduced pressure for 16 h. The surface concentration ($\mu mol/m^2$) of dialkylsilyl and alkylsilyl groups was determined by the difference in particle % C before and after the surface modification as measured by elemental analysis.

A secondary surface modification or end capping reaction was run using a second silane, including chlorotrimethylsilane, chlorotriethylsilane, and tert-butyldimethylchlorosilane (all from Aldrich Chemical), following the above procedure with respect to reagent amounts and reaction conditions. Table 7 lists the unmodified hybrid particle composition, the chemical formula of the first silane, the chemical formula of the second or end capping silane, the surface concentration of the first silane bonded phase, and total % C for selected final modified particles. Silanes and their sources were as follows: octadecyltrichlorosilane (Aldrich Chemical); octadecylmethyldichlorosilane, (3-phenyl- Example 25

Selected examples of surface derivatized hybrid silicas from Example 23 were used for the separation of a mixture of neutral, polar and basic compounds listed in Table 8. The 3.9×150 mm chromatographic columns were packed using a slurry packing technique. The HPLC system consisted of an Alliance 2690 XE separations module, a model 996 photodiode array detector, a Millennium[32] v. 2.15.01 data management system (all from Waters Corporation, Milford, Mass.), and a NESLAB RTE-111 circulating water bath for column temperature control (NESLAB Instruments, Inc., Portsmouth, N.H.). Mobile phase conditions were: 20 mM $KH_2PO_4/K_2HPO_4$, pH 7.0/methanol (35:65 v/v); flow rate: 1.0 mL/min; temperature: 23.4° C.; detection: 254 nm.

TABLE 8

|  | Product 19b in Table 6 | Product 19c in Table 6 | Product 19d in Table 6 |
|---|---|---|---|
| k of Acenaphthene | 10.02 | 11.35 | 13.40 |
| Relative Retention (r) | | | |
| Propranolol/Acenaphthene | 0.157 | 0.149 | 0.139 |
| Butyl paraben/Acenaphthene | 0.226 | 0.216 | 0.223 |
| Dipropyl Phthalate/Acenaphthene | 0.411 | 0.405 | 0.403 |
| Naphthalene/Acenaphthene | 0.437 | 0.436 | 0.437 |
| Amitriptyline/Acenaphthene | 1.483 | 1.525 | 1.395 |

It can be seen that the packing materials based on the hybrid materials provide ample retention and resolution in the separation of neutral, polar, and basic compounds. (Relative retention is the (k of the analyte) divided by the (k of acenaphthene). Therefore values less than one, indicate less retention than acenaphthene, and values greater than one, indicate more retention than acenaphthene. Relative retention is a well known parameter in the field of HPLC.)

Example 26

Selected examples of surface derivatized hybrid materials from Examples 24 and 25 as well as similarly derivatized commercial columns based on silica which have similar alkyl silyl groups were evaluated for basic compound USP peak tailing factors using the mobile phase and test conditions of Example 25. The results are shown in Table 9.

TABLE 9

|  | USP Tailing Factors | |
|---|---|---|
| Column | Propranolol | Amitriptyline |
| Commercial Column A ($C_{30}$ Type) | 1.6 | 3.6 |
| Example 23j ($C_{30}$ Type) | 1.3 | 2.3 |
| Commercial Column C ($C_{18}$ Type) | 4.2 | 7.0 |
| Commercial Column D ($C_{18}$ Type) | 1.3 | 1.8 |
| Commercial Column E ($C_{18}$ Type) | 1.0 | 1.7 |
| Commercial Column F ($C_{18}$ Type) | 1.3 | 1.5 |
| Example 23b ($C_{18}$ Type) | 1.1 | 1.0 |
| Example 23c ($C_{18}$ Type) | 1.0 | 1.4 |
| Example 23d ($C_{18}$ Type) | 1.0 | 1.4 |
| Example 24a ($C_{18}$ Type) | 1.0 | 1.3 |
| Example 24h ($C_{18}$ Type) | 1.1 | 1.3 |
| Example 24i ($C_{18}$ Type) | 1.2 | 1.7 |
| Example 24u ($C_{18}$ Type) | 1.1 | 2.0 |
| Commercial Column I (Embedded Polar Type) | 1.3 | 1.3 |
| Example 23f (Embedded Polar Type) | 1.1 | 1.2 |
| Example 23l (Embedded Polar Type) | 1.0 | 1.1 |
| Commercial Column J ($C_8$ Type) | 1.1 | 1.3 |
| Commercial Column K ($C_8$ Type) | 1.2 | 1.4 |
| Example 23k ($C_8$ Type) | 1.1 | 1.3 |
| Commercial Column L (Ph Type) | 1.8 | 3.9 |
| Commercial Column M (Ph Type) | 2.1 | 1.6 |
| Example 23h (Ph Type) | 1.3 | 1.2 |
| Example 24c (Ph Type) | 1.2 | 1.4 |
| Example 24e (Ph Type) | 1.1 | 1.5 |
| Example 24f (Ph Type) | 1.0 | 1.3 |
| Commercial Column O ($C_6F_5$ Type) | 3.8 | 6.9 |
| Commercial Column P ($C_6F_5$ Type) | 1.3 | 4.2 |
| Example 23i ($C_6F_5$ Type) | 1.2 | 1.4 |
| Example 24m ($C_6F_5$ Type) | 2.3 | 1.8 |
| Commercial Column Q (CN type) | 1.7 | 3.0 |
| Example 24t (CN Type) | 1.2 | 1.4 |

It can be seen that the basic compound tailing factors on the packing materials based on the hybrid materials were generally lower than on the commercial silica-based materials (a lower value corresponds to reduced tailing).

Example 27

Selected examples of surface derivatized hybrid silicas from Examples 24 and 25 as well as similarly derivatized commercial columns based on silica gel which have similar alkyl silyl groups were evaluated for stability in alkaline mobile phases using the following procedure. Columns were prepared by slurry packing the materials into 4.6×150 mm steel columns, and the analysis conditions were as follows: 1) The plate number, N, (5 sigma method) was measured for a test analyte, acenaphthene. Mobile phase conditions were acetonitrile-20 mM $KH_2PO_4/K_2HPO_4$ pH 7.00 (40:60, v/v) at a flow of 1.0 mL/min and a column temperature of 50.0° C. 2) The column was purged with 50 mM triethylamine pH 10.00 mobile phase and run for 15 min in the 50 mM triethylamine pH 10.00 mobile phase at a flow of 2.0 mL/min and a column temperature of 50.0° C. 3) In 15 min increments, the column was purged with 100% water (10 minutes at 2.0 mL/minute) and then purged with 100% methanol (10 minutes at 2.0 mL/minute). 4) The column was then purged and equilibrated with the mobile phase of step 1 above, and N for acenaphthene was measured. 5) The process was then repeated starting at step 2. Packed columns were kept in a 50° C. water bath throughout the test. Column lifetime is defined as the time of exposure to the pH 10 triethylamine solution when the efficiency of the column drops to 50% of its initial value. The results are shown in Table 10.

TABLE 10

| Column | Lifetime (h) |
|---|---|
| Commercial Column A ($C_{30}$ Type) | 17 |
| Example 23j ($C_{30}$ Type) | 57 |
| Commercial Column C ($C_{18}$ Type) | 18 |
| Commercial Column D ($C_{18}$ Type) | 17 |
| Commercial Column E ($C_{18}$ Type) | 28 |
| Commercial Column F ($C_{18}$ Type) | 23 |
| Commercial Column G ($C_{18}$ Type) | 23 |
| Example 23a ($C_{18}$ Type) | 51 |
| Example 23c ($C_{18}$ Type) | 48 |
| Example 23d ($C_{18}$ Type) | 50 |
| Example 24a ($C_{18}$ Type) | 36 |
| Example 24h ($C_{18}$ Type) | 41 |
| Example 24i ($C_{18}$ Type) | 34 |
| Example 24u ($C_{18}$ Type) | >153 |
| Example 24x ($C_{18}$ Type) | 41 |
| Commercial Column I (Embedded Polar Type) | 29 |
| Example 23f (Embedded Polar Type) | 32 |
| Example 23l (Embedded Polar Type) | 303 |
| Commercial Column J ($C_8$ Type) | 18 |

TABLE 10-continued

| Column | Lifetime (h) |
|---|---|
| Commercial Column K ($C_8$ Type) | 13 |
| Example 23k ($C_8$ Type) | 26 |
| Commercial Column L (Ph Type) | 20 |
| Commercial Column M (Ph Type) | 16 |
| Example 23h (Ph Type) | 29 |
| Example 24c (Ph Type) | 25 |
| Example 24e (Ph Type) | 26 |
| Example 24f (Ph Type) | 29 |
| Commercial Column O ($C_6F_5$ Type) | 14 |
| Commercial Column P ($C_6F_5$ Type) | 6 |
| Example 23i ($C_6F_5$ Type) | 24 |
| Example 24m ($C_6F_5$ Type) | 18 |
| Commercial Column Q (CN type) | 5 |
| Example 24t (CN Type) | 9 |

It is evident that the lifetimes of the columns containing hybrid packing materials are greatly improved over the commercial columns containing silica-based materials.

Incorporation By Reference

The entire contents of all patents, published patent applications and other references cited herein are hereby expressly incorporated herein in their entireties by reference.

Equivalents

Those skilled in the art will recognize, or be able to ascertain using no more than routine experimentation, numerous equivalents to the specific procedures described herein. Such equivalents were considered to be within the scope of this invention and are covered by the following claims. The contents of all references, issued patents, and published patent applications cited throughout this application are hereby incorporated by reference.

What is claimed is:

1. A porous inorganic/organic hybrid material, comprising porous inorganic/organic hybrid particles having a chromatographically-enhancing pore geometry, wherein said particles have been surface modified with a surface modifier having the formula $Z_a(R')_b Si—R$, where Z=Cl, Br, I, $C_1$–$C_5$ alkoxy, dialkylamino or trifluoromethanesulfonate; a and b are each an integer from 0 to 3 provided that a+b=3; R' is a $C_1$–$C_6$ straight, cyclic or branched alkyl group, and R is a functionalizing group.

2. The hybrid material of claim 1, wherein said particles have been further surface modified by coating with a polymer.

3. The hybrid material of claim 1 wherein R' is selected from the group consisting of methyl, ethyl, propyl, isopropyl, butyl, t-butyl, sec-butyl, pentyl, isopentyl, hexyl and cyclohexyl.

4. The hybrid material of claim 1 wherein the functionalizing group R is selected from the group consisting of alkyl, alkenyl, alkynyl, aryl, cyano, amino, diol, nitro, ester, a cation or anion exchange group, and an alkyl or aryl group containing an embedded polar functionality.

5. The hybrid material of claim 4, wherein said functionalizing group R is a $C_1$–$C_{30}$ alkyl group.

6. The hybrid material of claim 4, wherein said functionalizing group R is a $C_1$–$C_{20}$ alkyl group.

7. The hybrid material of claim 1, wherein said surface modifier is selected from the group consisting of octyltrichlorosilane, octadecyltrichlorosilane, octyldimethylchlorosilane, and octadecyldimethylchlorosilane.

8. The hybrid material of claim 7, wherein said surface modifier is selected from the group consisting of octyltrichlorosilane and octadecyltrichlorosilane.

9. The hybrid material of claim 1, wherein said particles have been surface modified by a combination of organic group and silanol group modification.

10. The hybrid material of claim 1, wherein said particles have been surface modified by a combination of organic group modification and coating with a polymer.

11. The hybrid material of claim 1, wherein said particles have been surface modified by a combination of silanol group modification and coating with a polymer.

12. The hybrid material of claim 1, wherein said particles have been surface modified via formation of an organic covalent bond between the particle's organic group and the modifying reagent.

13. The hybrid material of claim 1, wherein said particles have been surface modified by a combination of organic group modification, silanol group modification, and coating with a polymer.

14. The hybrid material of claim 1, wherein said particles have been surface modified by silanol group modification.

15. A separations device having a stationary phase comprising porous inorganic/organic hybrid particles having a chromatographically-enhancing pore geometry, wherein the particles have been surface modified with a surface modifier having the formula $Z_a(R')_b Si—R$, where Z=Cl, Br, I, $C_1$–$C_5$ alkoxy, dialkylamino or trifluoromethanesulfonate; a and b are each an integer from 0 to 3 provided that a+b=3; R' is a $C_1$–$C_6$ straight, cyclic or branched alkyl group, and R is a functionalizing group.

16. The separations device of claim 15, wherein said surface modifier is selected from the group consisting of octyltrichlorosilane, octadecyltrichlorosilane, octyldimethylchlorosilane, and octadecyldimethylchlorosilane.

17. The separations device of claim 16, wherein said surface modifier is selected from the group consisting of octyltrichlorosilane and octadecyltrichlorosilane.

18. The separations device of claim 15, wherein said functionalizing group R is selected from the group consisting of alkyl, alkenyl, alkynyl, aryl, cyano, amino, diol, nitro, ester, a cation or anion exchange group, and an alkyl or aryl group containing an embedded polar functionality.

19. The separations device of claim 15, wherein said functionalizing group R is a $C_1$–$C_{30}$ alkyl group.

20. A chromatographic column having improved lifetime, comprising
   a) column having a cylindrical interior for accepting a packing material, and
   b) a packed chromatographic bed comprising porous inorganic/organic hybrid particles having a chromatographically-enhancing pore geometry that have been surface modified with a surface modifier having the formula $Z_a(R')_b Si—R$, where Z=Cl, Br, I, $C_1$–$C_5$ alkoxy, dialkylamino or trifluoromethanesulfonate; a and b are each an integer from 0 to 3 provided that a+b=3; R' is a $C_1$–$C_6$ straight, cyclic or branched alkyl group, and R is a functionalizing group.

21. A chromatographic column having improved lifetime, comprising
   a) column having a cylindrical interior for accepting a packing material, and
   b) a packed chromatographic bed comprising porous inorganic/organic hybrid particles having a chromatographically-enhancing pore geometry that have been surface modified with a surface modifier having the formula $Z_a(R')_b Si-R$, where Z=Cl, Br, I, $C_1$–$C_5$ alkoxy, dialkylamino or trifluoromethanesulfonate; a and b are each an integer from 0 to 3 provided that a+b=3; R' is a $C_{1-C6}$ straight, cyclic or branched alkyl group, and R is a functionalizing group.

* * * * *